United States Patent
Jiang

(10) Patent No.: US 8,524,466 B2
(45) Date of Patent: Sep. 3, 2013

(54) MICROVESICLE MEMBRANE PROTEIN AND APPLICATION THEREOF

(76) Inventor: Ming-Chung Jiang, New Taipei (CN)

( * ) Notice: Subject to any disclaimer, the term of this patent is extended or adjusted under 35 U.S.C. 154(b) by 0 days.

(21) Appl. No.: 13/443,462

(22) Filed: Apr. 10, 2012

(65) Prior Publication Data

US 2013/0045220 A1 Feb. 21, 2013

(30) Foreign Application Priority Data

Aug. 18, 2011 (WO) ................ PCT/CN2011/078559

(51) Int. Cl.
*G01N 33/574* (2006.01)

(52) U.S. Cl.
USPC .......................................... 435/7.23; 435/7.1

(58) Field of Classification Search
None
See application file for complete search history.

(56) References Cited

U.S. PATENT DOCUMENTS

| 8,211,659 B2 * | 7/2012 | Jiang et al. ................ | 435/7.23 |
| 2010/0120074 A1 * | 5/2010 | Jiang et al. ................ | 435/7.92 |
| 2010/0196426 A1 * | 8/2010 | Skog et al. ................ | 424/400 |

OTHER PUBLICATIONS

Tai et al., J. Exp Clin Cancer Res 2010; 29:110, pp. 1-9.*
Tsai et al., Am J Pathol 2010; 176(4): 1619-28.*
Scherf et al., Biochem Biophys Res Comm 1998; 250:623-28.*
Fendrick J.L., Konishi I., Geary S.M., Parmley T.H., Quirk J.G Jr., O'Brien T.J., "CA 125 Phosphorylation is Associated with It's Secretion from the WISH Human Amnion Cell Line", TumorBiology 1997, 18: 278-289.
Konishi I., Fendrick J.L., Parmley T.H., Quirk J.G. Jr., O'Brien T.J., "Epidermal Growth Factor Enhances Secretion of the Ovarian Tumor-Associated Cancer Antigen CA125 From the Human Amnion WISH Cell Line", J Soc Gynecol Invest, vol. 1, No. 1, Jan.-Mar. 1994.

* cited by examiner

*Primary Examiner* — Sheela J Huff
*Assistant Examiner* — Jessica H Roark
(74) *Attorney, Agent, or Firm* — McDonnell Boehnen Hulbert & Berghoff LLP

(57) ABSTRACT

Microvesicles play essential roles in disease progression. The present invention provides a microvesicle membrane protein and application thereof. Disclosed is method comprises phosphorylated CSE1L (cellular apoptosis susceptibility protein- or CSE1L-binding agents for microvesicle isolation, analysis, or binding for disease diagnosis or treatment.

9 Claims, 12 Drawing Sheets

MICROVESICLE MEMBRANE PROTEIN AND APPLICATION THEREOF

CROSS REFERENCE

This application relates to and claims the benefit of priority to International Application PCT/CN2011/078559, filed on Aug. 18, 2011, the disclosure of which is hereby incorporated by reference in its entirety.

FIELD OF THE INVENTION

The present invention relates to a phosphorylated CSE1L and application thereof, particularly for applying in microvesicle isolation, analysis, or binding for disease diagnosis or treatment.

BACKGROUND OF THE INVENTION

Accumulated studies have shown that microvesicles (microparticles) are involved in cell-to-cell communication by transfer of bioactive molecules including proteases, mRNAs, microRNAs, membrane receptors, and organelles among cells thus play essential physiological/pathological roles including the progression of various diseases such as coagulation diseases, wound healing, atherosclerosis, coronary diseases, diabetes, hematologic diseases, infectious diseases, inflammatory diseases, neurologic diseases, and metastasis of cancer (Simak et al. 2006; Cocucci et al. 2009; Muralidharan-Chari et al. 2010). Much interest centers on microvesicles and nanovesicles (exosomes) as they are increasingly cited as potential biomarkers. Microvesicles and exosomes are differentiated both by their size ranges and their biogenesis. Microvesicles are small, plasma-membrane-derived particles that are released into the extracellular environment by the outward budding and fission of the plasma membrane. Typically microvesicles are described as being 100 nm to 15 μm, whilst exosomes are in the range 30-100 nm. Microvesicles are typically formed by blebbing of the plasma membrane, whereas exosomes are released by exocytosis from multivesicular bodies of the endosome (Simak et al. 2006; Cocucci et al. 2009; Muralidharan-Chari et al. 2010).

Invasion and metastasis of tumor cells are the major cause of cancer-related morbidity and mortality. Tumor cells produce extracellular matrix (ECM)-degradation protease to degrade ECM for their invasion and metastasis. Microvesicles are plasma-membrane-derived particles and tumor-released microvesicles are rich in ECM-degradation proteases and thus play important role in the invasion and metastasis of cancer cells (Cocucci et al. 2009). The cellular signaling pathways that regulate microvesicle generation/shedding and cancer metastasis are not fully understood. Molecularly-targeted therapy is becoming a main stream in cancer therapy. The molecularly targeted drugs inhibit tumor progression by interrupting specific cellular signaling pathways that are abnormally activated in cancer cells. Therefore, identification of the cellular signaling that control the generation or release of microvesicle may facilitate finding of target for developing of targeted drugs for cancer, and may also facilitate the identification of biomarker that can conjunction with specific molecularly-targeted therapy for patient selection, monitoring, and management.

ERK (extracellular signal-regulated kinases) has been shown to mediate microvesicle shedding in tumor invasion (Muralidharan-Chari et al. 2009). Microvesicles need to be generated before being released outside cell membrane. However, little is known about the cellular signaling pathways that regulate microvesicle generation and cancer metastasis.

CSE1L (chromosome segregation 1-like protein), also named as CAS (cellular apoptosis susceptibility protein; GenBank accession no. U33286), is highly expressed in cancer and is involved in cancer invasion and metastasis (Brinkmann et al. 1995; Tung et al. 2009; Tai et al. 2010). CSE1L has previously been shown to be a cellular tyrosine phosphorylated protein that is phosphorylated by MEK (mitogen-activated protein kinase or extracellular signal-regulated kinase) and this is related with the nuclear transport of CSE1L (Scherf et al. 1998). Microvesicles produced by tumor cells play important role in cancer metastasis (Muralidharan-Chari et al. 2010).

The ERK signaling pathway is involved in the proliferation, survival, invasion and metastasis of cancer cells (Roberts et al. 2007). Aberrant activation of the ERK pathway has been shown to be an essential feature common to many types of human tumors (Hoshino et al. 1999). The present invention discloses that CSE1L is linked to ERK signaling pathway, CSE1L is phosphorylated upon ERK activation, phosphorylated CSE1L is present in sera from cancer patients, and assay of serum phosphorylated CSE1L is superior to assay of serum CSE1L for cancer diagnosis. Therefore, serum phosphorylated CSE1L should have clinical utility in cancer diagnosis.

The Ras-ERK pathway is a potential targets for development of molecularly-targeted drug for cancer therapy (Roberts et al. 2007).

A significant limitation in molecularly-targeted therapy is that not all patients can receive targeted therapy since the patient's tumor may not express the target that the therapy is being directed to. Also, tumor-related mortalities still occur in targeted therapy due to the proliferation of the "target-negative" tumor cell population. Shedding microvesicles of specific composition may be loaded with drugs addressed with high precision to unique cellular targets (Cocucci et al. 2009). Microvesicles generation/shedding should be the common feature occurs in tumors (Simak et al. 2006; Cocucci et al. 2009; van Doormaal et al. 2009; Muralidharan-Chari et al. 2010).

U.S. Pat. No. 6,664,057 disclosed the identification of a novel amplicon on human chromosome 20q13.2 which is associated with cancer. U.S. Pat. No. 6,072,031 disclosed the cDNA and amino acid sequences for the cellular apoptosis susceptibility protein are used to detect expression and amplification of the CSE1L gene in normal and cancer cells. An antisense CSE1L gene sequence introduced into living cells inhibits CSE1L protein activity and thus prevents or inhibits apoptosis in the cells. U.S. Pat. No. 5,759,782 disclosed the cDNA and amino acid sequences for the cellular apoptosis susceptibility protein are used to detect expression and amplification of the CSE1L gene in normal and cancer cells. An antisense CSE1L gene sequence introduced into living cells inhibits CSE1L protein activity and thus prevents or inhibits apoptosis in the cells. U.S. Pat. No. 6,207,380 claims assay of polypeptides and polynucleotides in urinary tract tissue and is useful for detecting, diagnosing, staging, monitoring, prognosticating, in vivo imaging, preventing or treating, or determining the predisposition of an individual to diseases and conditions of the urinary tract. These sequences are derived from keratin cytokeratin, CSE1L, or mat-8 polypeptides and polynucleotides. U.S. Pat. No. 6,207,380 also provided are antibodies that specifically bind to keratin cytokeratin, CSE1L, or mat-8-encoded polypeptides or proteins in the urinary tract tissue, which molecules are useful for the therapeutic treatment of urinary tract diseases. Thus, U.S. Pat. No.

6,207,380 disclose using antibodies that specifically bind to keratin cytokeratin, CSE1L, or mat-8 in the urinary tract tissue for the therapy of urinary tract diseases. U.S. Pat. No. 6,232,086 disclose the cDNA and amino acid sequences for a CSE1L protein that can be used to detect expression and amplification of the CSE1L gene in normal and cancer cells. U.S. Pat. No. 6,156,564 disclose a method of detecting human proliferating cells comprising measuring a level of a human CSE1L protein in a human cell sample and detecting the human CSE1L protein at a level at least two-fold greater than the level of a human CSE1L protein in normal non-proliferating human cells. U.S. Pat. No. 6,440,737 disclose antisense compounds, compositions and methods for modulating the expression of CSE1L gene. The disclosure of US20080081339 describes measuring dozens of autoantibodies including CSE1L autoantibody (not antigens or tumor associated marker) present in a body fluid as biomarkers for prostate cancer diagnosis. The disclosure of US20050260639 describes determining the expression level of pancreatic cancer-associated gene including CSE1L in circulation cancer cells isolated from bodily fluid or bodily tissue for detecting and diagnosing pancreatic cancer. Based on the result of a cDNA gene chip, the disclosure of WO2009/052573 describes isolating hundreds of RNA transcripts including CSE1L transcript (i.e. CSE1L mRNA) from circulation tumor cells in blood sample or tissue to assay the onset of an adenoma state of gastrointestinal cancer. The disclosure of US20100120074 describes the measurement of CSE1L or CSE1L polypeptide levels in the body fluids for metastatic cancer diagnosis. US20110053157 describes the measurement of nucleic acids including DNA, RNA, and microRNA in microvesicles (exosomes) for diagnosis, prognosis and treatment of medical diseases and conditions. US20110053157 describes methods of aiding diagnosis, prognosis, monitoring and evaluation of a disease or other medical condition in a subject by detecting a DNA or RNA biomarker in microvesicles isolated from a biological sample from the subject; method of delivering a nucleic acid or protein to a target all by administering microvesicles that contain said nucleic acid or protein; methods for performing a body fluid transfusion by introducing a microvesicle-free or microvesicle enriched fluid fraction into a patient. WO2009021322 and US20100255514 describe method for diagnosis and prognosis of cancer and for monitoring the progression of cancer and/or the therapeutic efficacy of an anti-cancer treatment in a sample of a subject by detecting selected oncogenic proteins consisting of EGFRvIII, EGFR, HER-2, HER-3, HER-4, MET, cKit, PDGFR, Wnt, beta-catenin, K-ras, H-ras, N-ras, Raf, N-myc, c-myc, IGFR, PI3K, Akt, BRCA1, BRCA2, PTEN, and receptors of cells associated with cancer (cancer-related receptors) such as VEGFR-2, VEGFR-1, Tie-2, TEM-1 and CD276 in microvesicles. The prior arts above detect the expression of CSE1L gene in cell level or CSE1L protein level in the body fluids. Therefore, none of the references describes or claim CSE1L or phosphorylated CSE1L binding agents, such as anti-CSE1L antibody or anti-phosphorylated CSE1L antibody and derivatives as well as pharmaceutical compositions and kits comprised the antibodies or derivative for detecting CSE1L or phosphorylated CSE1L in microvesicles or fluids from biological samples. Also, no prior arts disclosed, described, or claimed methods for the treatment and prevention of diseases comprised administering to a subject the CSE1L-binding agent or the phosphorylated CSE1L-binding agent. Also, no references disclosed, described, or claimed methods and kit comprising CSE1L-binding agent or phosphorylated CSE1L-binding agent for microvesicle isolation, analysis, or targeting for disease diagnosis or treatment.

SUMMARY OF THE INVENTION

In general, the invention discloses novel method comprising antibodies against CSE1L or phosphorylated CSE1L for microvesicle isolation, analysis, or binding for disease diagnosis or treatment. One aspect of the invention provides a method for diagnosing the presence or progressing of a disease in a subject, the method comprising: (a) determining the level of CSE1L or phosphorylated CSE1L in microvesicles in biological fluid sample from an subject; (b) determining the level of CSE1L or phosphorylated CSE1L in microvesicles in biological fluid sample from the normal subjects as the control; and (c) diagnosing the presence or progressing of a disease in the subject based upon the presence of a difference in CSE1L or phosphorylated CSE1L level in microvesicles in biological fluid sample of the subject, as compared to that of the control subjects.

Another aspect of the invention provides a method for diagnosing the presence or progressing of cancer in a subject, the method comprising: (a) determining the level of phosphorylated CSE1L in biological fluid sample from a subject; (b) determining the level of phosphorylated CSE1L in biological fluid sample from the normal subject as the control; and (c) diagnosing the presence or progressing of cancer in the subject based upon the presence of a difference in phosphorylated CSE1L level in the biological fluids of the subject, as compared to that of the control subjects.

A further aspect of the invention provides a method for isolating microvesicles from a biological fluid sample, the method comprising: (a) contacting the biological fluid sample with an antibody against CSE1L or phosphorylated CSE1L; and (b) isolating microvesicles bound by the antibody.

Yet another aspect of the invention provides a method for detecting the presence of microvesicles in a biological fluid sample, the method comprising: (a) contacting the biological fluid sample with antibody against CSE1L or phosphorylated CSE1L; and (b) detecting the binding of the antibody to microvesicles.

Another aspect of the invention provides a method comprising administering antibodies against CSE1L or phosphorylated CSE1L to bind microvesicles for disease prevention or disease treatment. Particularly preferred disease is cancer.

Another aspect of the invention provides a pharmaceutical composition comprising antibodies against CSE1L or phosphorylated CSE1L that binds microvesicles for disease diagnosis or treatment. Particularly preferred disease is cancer.

Other objects, features, and advantages of the present invention will be apparent to one of skill in the art from the following detailed description and figures.

DETAILED DESCRIPTION OF THE INVENTION

Figure 1:
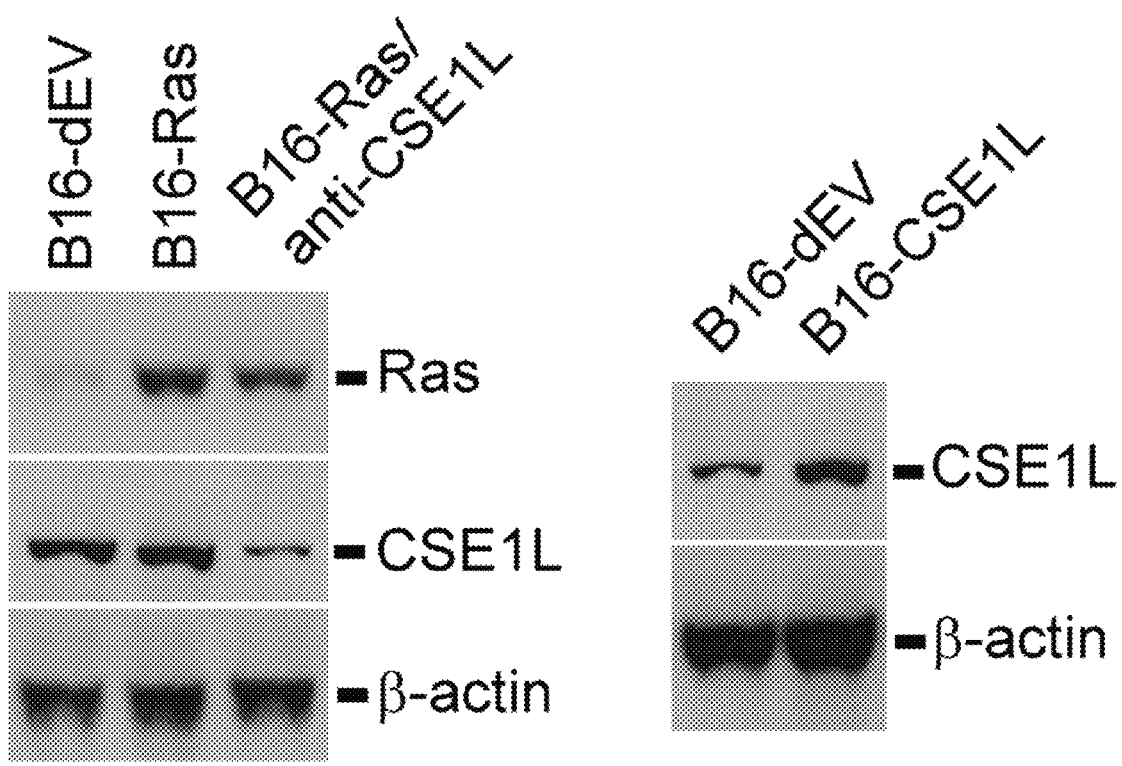
FIG. 1 refers to immunoblot analyses of the levels of Ras and CSE1L in B16-dEV, B16-Ras cells, B16-CSE1L, and B16-Ras/anti-CSE1L cells. β-Actin levels were assayed as a control. B16F10 melanoma cell were stably transfected with the control plasmids, v-H-ras expressing plasmids, CSE1L expressing plasmids, or v-H-ras expressing plasmids plus CSE1L shRNA expressing plasmids, to obtain the B16-dEV, B16-Ras, B16-CSE1L, and B16-Ras/anti-CSE1L cells, respectively.

Microvesicles (sometimes called circulating microvesicles, microparticles, or exosomes) are fragments of plasma membrane shed from cells. Microvesicles can be found in body fluids and cell culture conditioned media. Microvesicles can be released into the body fluids or the cell culture conditioned media as the free microvesicles; microvesicles may also not be released and are associated with the membrane of a cell as the cell membrane-associated microvesicles (Simak et al. 2006; Cocucci et al. 2009; Muralidharan-Chari et al. 2010). The methods and compositions described herein are equally applicable to free microvesicles and cell membrane-associated microvesicles. Typically microvesicles are described as being 100 nm to 15 µm, whilst exosomes are in the range 30-100 nm. The methods and compositions described herein are equally applicable to microvesicles of all sizes.

Certain aspects of the present invention are based on the surprising finding that CSE1L mediates the generation of microvesicles, CSE1L is localized in microvesicle membrane, CSE1L is a serine/threonine and tyrosine phosphorylated protein, and phosphorylated CSE1L is present in the sera of cancer patients. Accumulated studies have shown that microvesicles are involved in cell-to-cell communication by transfer of bioactive molecules including proteases, mRNAs, microRNAs, membrane receptors, and organelles among cells thus play essential physiological/pathological roles including the progression of various diseases such as coagulation diseases, wound healing, atherosclerosis, coronary diseases, diabetes, hematologic diseases, infectious diseases, inflammatory diseases, neurologic diseases, and cancer (Simak et al. 2006; Cocucci et al. 2009; Muralidharan-Chari et al. 2010). Thus, microvesicle proteins especially microvesicle proteins that localized in microvesicle membrane are valuable biomarkers for disease diagnosis. Also, agents that can bind with microvesicle membrane protein can be use for medical imaging or disease treatment.

Another surprising finding in the present invention is that CSE1L is linked to ERK signaling pathway, CSE1L is phosphorylated upon ERK activation, phosphorylated CSE1L is present in sera from cancer patients, and assay of serum phosphorylated CSE1L is superior to assay of serum CSE1L for cancer diagnosis (Example 14). Aberrant activation of the ERK pathway has been shown to be an essential feature common to many types of human tumors (Hoshino et al. 1999). Therefore, level of phosphorylated CSE1L definitely will be higher in sera from cancer patients than that from healthy individuals. Also, assay of serum phosphorylated CSE1L definitely will be more sensitive than assay of serum CSE1L for cancer diagnosis. Thus, phosphorylated CSE1L should have clinical utility in cancer diagnosis.

Another surprising finding in the present invention is that CSE1L is linked to Ras-ERK signaling and cancer metastasis. The Ras-ERK pathway is a potential targets for development of molecularly-targeted drug for cancer (Roberts et al. 2007). CSE1L is linked to Ras-ERK signaling and cancer metastasis. And phosphorylated CSE1L is presence in the sera of cancer patients. Therefore, serum phosphorylated CSE1L may have clinical utility in conjunction with specific molecularly-targeted therapy for patient selection, monitoring, and management.

The other surprising finding in the present invention is that CSE1L is localized in microvesicle membrane, and anti-CSE1L antibodies can target tumor. The shedding microvesicles are widespread on the membrane of tumor cells and the shed microvesicles may remain in the extracellular environment around tumor cells; hence, microvesicle membrane proteins may be the potential targets for cancer therapy. Therefore, the localization of CSE1L in microvesicle membrane indicates that CSE1L may be a therapeutic target for cancer. A significant limitation in molecularly-targeted therapy is that not all patients can receive targeted therapy since the patient's tumor may not express the target that the therapy is being directed to. Also, tumor-related mortality may still occur in targeted therapy due to the proliferation of the "target-negative" tumor cell population. Shedding microvesicles of specific composition may be loaded with drugs addressed with high precision to unique cellular targets (Cocucci et al. 2009). Microvesicles generation/shedding should be the common feature occurs in tumors (Simak et al. 2006; Cocucci et al. 2009; van Doormaal et al. 2009; Muralidharan-Chari et al. 2010). Therefore, CSE1L may be a potential target for the development of targeted therapy for most cancer patients.

Certain aspects of the present invention are based on the finding that microvesicles are released from tumor cells and circulating in bodily fluids. The number of microvesicles increases as the tumor grows. The concentration of the microvesicles in bodily fluids is proportional to the corresponding tumor load. The bigger the tumor load, the higher the concentration of microvesicles in bodily fluids.

Certain aspects of the present invention are based on another surprising finding that CSE1L and phosphorylated CSE1L are present in microvesicles. The other surprising finding in the present invention is that phosphorylated CSE1L are present in bodily fluid of a subject.

Certain aspects of the present invention are based on another surprising finding that CSE1L and phosphorylated CSE1L are microvesicle membrane protein.

Another aspect of the present invention relates to methods or kits for isolation or analysis of microvesicles from the body fluid. Based on the finding that CSE1L and phosphorylated CSE1L are microvesicle membrane protein. And microvesicles play essential physiological/pathological roles including the progression of many diseases. Methods or kits comprising CSE1L-binding agent or phosphorylated CSE1L-binding agent can be use for capture, purified, isolation, detection, or analysis the microvesicles from the body fluid or any biological samples such as culture conditioned media. Methods or kits comprising CSE1L-binding agent or phosphorylated CSE1L-binding agent for microvesicle isolation or analysis for which the inventions described herein are applicable include, but are not limited to, for example ultracentrifugation, immunoprecipitation, affinity purification, microfiltration, FACS (fluorescence activated cell sorter), ELISA (enzyme-linked immunosorbent assay), microarray, biochips, chromatography, Western blotting, microfluidic systems, microfluidic chip, and other techniques involving immunological binding.

In another preferred embodiment of the invention, the detection or analysis of microvesicles is performed using an optical method. Any optical method may be used. Preferred optical methods comprise microscopy, confocal microscopy, fluorescence microscopy, internal reflection fluorescence microscopy, ellipsometry/reflectometry, light scattering or surface plasmon microscopy.

Certain aspects of the present invention are based on the surprising finding that CSE1L and phosphorylated CSE1L are microvesicle membrane protein and CSE1L-binding agent or phosphorylated CSE1L-binding agent such as anti-CSE1L antibodies can target tumor as shown in Example 10. Methods or kits comprising CSE1L-binding agent or phosphorylated CSE1L-binding agent can be use for medical imaging of disease.

Certain aspects of the present invention are based on the surprising finding that CSE1L and phosphorylated CSE1L are microvesicle membrane protein and CSE1L-binding agent or phosphorylated CSE1L-binding agent such as anti-CSE1L antibodies can target tumor as shown in Example 10. Methods or kits comprising CSE1L-binding agent or phosphorylated CSE1L-binding agent conjugated with a therapeutic agents or cytotoxic agent, as well as pharmaceutical compositions and kits comprising CSE1L-binding agent or phosphorylated CSE1L-binding agent can be use for disease treatment.

One aspect of the present invention relates to methods and kits for diagnosing or monitoring a disease in a subject by determining the amount of CSE1L or phosphorylated CSE1L in microvesicles or in fluids obtained from a biological sample. The determination may be performed using the biological sample without first isolating the microvesicles or by isolating the microvesicles first.

Another aspect of the present invention relates to methods or kits for diagnosing or monitoring a disease or other medical condition in a subject comprising the steps of isolating microvesicles from a bodily fluid of a subject, and analyzing CSE1L or phosphorylated CSE1L in the microvesicles. The CSE1L or phosphorylated CSE1L are analyzed qualitatively and/or quantitatively, and the results are compared to results expected or obtained for one or more other subjects who have or do not have the disease or other medical condition as the controls. The presence of a difference in microvesicular CSE1L or microvesicular phosphorylated CSE1L content of the subject, as compared to that of the controls, can indicate the presence or absence of, the progression of (e.g., changes of tumor size and tumor malignancy), or the susceptibility to a disease or other medical condition in the subject.

Another aspect of the present invention relates to methods or kits for diagnosing or monitoring a disease or other medical condition in a subject comprising the steps of collecting biological fluids of a subject, and analyzing phosphorylated CSE1L in the biological fluids. The phosphorylated CSE1L are analyzed qualitatively and/or quantitatively, and the results are compared to results expected or obtained for one or more other subjects who have or do not have the disease or other medical condition as the controls. The presence of a difference in phosphorylated CSE1L content of the subject, as compared to that of the controls, can indicate the presence or absence of, the progression of (e.g., changes of tumor size and tumor malignancy), or the susceptibility to a disease or other medical condition in the subject.

Microvesicles play essential pathological roles in the progression of various diseases. Diseases or other medical conditions for which the inventions described herein are applicable include, but are not limited to, coagulation diseases, atherosclerosis, coronary diseases, diabetes, hematologic diseases, inflammatory diseases, neurologic diseases, autoimmune diseases, infectious diseases, and cancer. The elevation of circulating microvesicles has been demonstrated in plasma of patients with exacerbated multiple sclerosis (MS). In these patients, microvesicles defined as of endothelial origin were significantly increased when compared with healthy control subjects (Simak et al. 2006). Elevation of circulating microvesicles was also documented in acute cerebrovascular syndromes. An increase of platelet microvesicles was shown in patients with transient ischemic attacks and lacunar infarcts (Simak et al. 2006). In coagulation diseases, endothelial cell membrane microparticles (microvesicles) were found elevated in patients with coronary artery disease when compared with healthy control subjects (Simak et al. 2006). The association of MPs in blood with high blood pressure or postprandial triglyceridemia was also studied. Both endothelial CD31-positive/CD42-negative microvesicles and platelet CD41-positive microvesicles were significantly elevated in patients with severe hypertension (Simak et al. 2006). A role of microvesicles-facilitated intercellular transport of CD81, a co-receptor in B- and T-cell activation and a candidate receptor for hepatitis C virus infection, has been indicated in immunomodulation of hepatitis C virus infection (Simak et al. 2006). Microparticles may influence sensitivity of cells to pathogens such as HIV-1 by facilitating intercellular transfer of specific receptors. The chemokine receptor CCR5, the principal coreceptor for macrophage-tropic HIV-1, can be released through (microvesicles) from the surface of CCR5-positive peripheral blood mononuclear cells. Microparticles containing CCR5 can transfer this receptor to CCR5-negative cells and render them CCR5-positive. The CCR5 transfer to CCR5 peripheral blood mononuclear cells enabled infection of these cells with macrophage-tropic HIV-1 (Simak et al. 2006). Platelet microvesicles were elevated in patients with type 2 diabetes mellitus (Simak et al. 2006). Especially, monocyte microvesicles were highly elevated in patients with diabetic nephropathy and could be an indication of vascular complications in diabetes (Simak et al. 2006). Sustained elevated amounts of circulating procoagulant platelet microvesicles after acute myocardial infarction in diabetic patients, which were higher than in myocardial infarction nondiabetic patients (Simak et al. 2006). Microvesicles in blood have been extensively studied in thrombotic thrombocytopenic purpura, a hematologic disease. Elevated platelet microvesicles associated with calpain activity have been documented in plasma of patients with thrombotic thrombocytopenic purpura (Simak et al. 2006). Indeed, endothelial microvesicles in blood from patients with acute thrombotic thrombocytopenic purpura showed counts markedly elevated compared with healthy control subjects, but values returned to normal in remission (Simak et al. 2006). Also, it was shown that red blood cells from patients with paroxysmal nocturnal hemoglobinuria released significantly fewer microvesicles in vitro upon stimulation with a calcium ionophore when compared with healthy control subjects (Simak et al. 2006). In patients with stage IV gastric cancer, platelet microvesicles were significantly elevated when compared with patients with stage I or II/III. Platelet microvesicles count had also more than 90% sensitivity and specificity in the prediction of distant metastasis in these patients (Simak et al. 2006). In inflammatory diseases and autoimmune diseases, a possible use of endothelial microvesicle for the diagnosis and monitoring of activity in the systemic vasculitis was found (Simak et al. 2006). Another example is rheumatoid arthritis where elevated levels of platelet microvesicle in blood were associated with the rheumatoid arthritis disease activity (Simak et al. 2006). Elevated microvesicle of endothelial origin, were found in patients with lupus anticoagulant (Simak et al. 2006).

The present invention also discloses methods for cancer diagnosis and treatment. A "cancer" in an animal refers to the presence of cells possessing characteristics typical of cancer-causing cells, such as uncontrolled proliferation, immortality, metastatic potential, rapid growth and proliferation rate, and certain characteristic morphological features and cellular markers. In some circumstances, cancer cells are in the form of a tumor, but they may also exist alone within an animal, or circulate in the blood stream as independent cells, such as leukemic cells. Cancer can be any kind of cancer. Examples of different types of cancer include, but are not limited to, lung cancer (e.g., non-small cell lung cancer); digestive and gastrointestinal cancers such as colorectal cancer, gastrointestinal stromal tumors, gastrointestinal carcinoid tumors, colon cancer, rectal cancer, anal cancer, bile duct cancer, small intestine cancer, and stomach (gastric) cancer; esophageal cancer; gallbladder cancer; liver cancer; pancreatic cancer; appendix cancer; breast cancer; ovarian cancer; renal cancer (e.g., renal cell carcinoma); cancer of the central nervous system; skin cancer; lymphomas; choriocarcinomas; head and neck cancers; osteogenic sarcomas; and blood cancers. As used herein, a "tumor" comprises one or more cancerous cells.

The present invention also discloses detection of phosphorylated CSE1L by binding of an antibody that specifically recognizes phosphorylated CSE1L protein. The phosphorylated CSE1L can be serine phosphorylated CSE1L, threonine phosphorylated CSE1L, or tyrosine phosphorylated CSE1L. The antibodies can be chimeric, humanized, or fully human antibodies. The antibodies can be monoclonal antibodies, polyclonal antibodies, a single-chain antibody, a single chain Fv antibody, an Fab antibody, an Fab' antibody, an (Fab')$_2$ antibody, or a fully human antibody.

The microvesicles in biological fluid samples. As used herein, "biological fluid samples" refers to a sample of fluid isolated from anywhere in the body of the subject, including but not limited to, for example, blood, serum, plasma, urine, lymph fluid, spinal fluid, sputum, pleural fluid, fine needle aspirate, nipple aspirates, fluid of the respiratory, intestinal, and genitourinary tracts, breast milk, tear fluid, saliva, fluid from the lymphatic system, semen, intra-organ system fluid, cerebrospinal fluid, ascitic fluid, amniotic fluid, and tumor cyst fluid. "Biological fluid samples" also refers to culture conditioned media and cells in the culture conditioned media. Particularly preferred biological samples are blood, urine, and conditioned media. Microvesicles in biological fluid sample also refer to microvesicles that are associated with the membrane of a cell that is presented in the biological fluid sample. Conditioned media is media that cells have been cultured in for a period of time as opposed to media fresh out of the bottle.

The term "subject" refers to all animals shown to or expected to have microvesicles. The animal includes a mammal, and preferably a human.

The term "normal subject" refers to the subject that is free of cancer or other diseases.

A "test" subject is a subject being tested.

The term "medical condition" refers to the condition of a disease in the body of an organism.

The term "immunological techniques" refers to any assay involving antibody-based detection techniques including, without limitation, dot blot, Western blotting, immunoprecipitation, and direct and competitive ELISA and RIA techniques.

As used herein, "dot blot" refers to an analytical procedure in which a sample are attached to and immobilized in single-stranded form on the surface of a paper, glass fiber, or plastic sheet and the presence of the protein is determined by various methods which may create visible signals, including hybridization to a directly or indirectly labeled antibody.

The term "tumor targeting" refers to the ability of a compound to preferentially associate with tumors (e.g., cancerous, pre-cancerous, and/or benign). A tumor targeting pharmaceutical composition is pharmaceutical composition which preferentially binds to or associates with tumor tissues, as compared to non-tumor tissues.

The term "medical imaging" refers to the technique and process used to create images of the human body for clinical purposes (medical procedures seeking to reveal, diagnose, or examine disease) or medical science (including the study of normal anatomy and physiology in animal models of research).

A "therapeutic agent" is an agent that exerts a cytotoxic, cytostatic, or immunosuppressive effect on cancer cells.

A "cytotoxic effect" refers to the depletion, elimination and/or the killing of a target cell. A "cytotoxic agent" refers to an agent that has a cytotoxic effect on a cell.

The term "antibody" as used herein refers to (a) immunoglobulin polypeptides and immunologically active portions of immunoglobulin polypeptides (i.e., polypeptides of the immunoglobulin family, or fragments thereof, that contain an antigen binding site that immunospecifically binds to a specific antigen (e.g., CSE1L), or (b) conservatively substituted derivatives of such immunoglobulin polypeptides or fragments that immunospecifically bind to the antigen (e.g., CSE1L).

The antibodies can be generated by methods known in the art. For example, monoclonal antibodies can be prepared using a wide variety of techniques including, e.g., the use of hybridoma, recombinant, and phage display technologies, or a combination thereof.

"Cancer therapy" refers to the technique, process, or substance that can control the growth, invasion, metastasis, or mortality of cancer.

The binding reaction between microvesicles and the CSE1L antibodies or phosphorylated CSE1L antibodies can be detected using immunoassay principles. In typical immunoassays, either protein or antibody is immobilized and detection is achieved after separating un-reacted components. Methods for immobilizing cells or antibodies are known. For example, they can be immobilized directly onto solid phase by chemical linking or physical adsorption. Alternatively, when an antibody of the present invention is biotinylated, it is also possible to indirectly immobilize the antibody onto a solid phase which has adsorbed avidin, streptavidin, or the like. When an antibody is bound to magnetic particles, not only the antibody but also cells bound to the antibody can be quickly and conveniently detected and isolated using a magnet. Alternatively, when using an antibody that recognizes multiple antigens, such as a multispecific antibody, the antibody is bound to CSE1L or phosphorylated CSE1L on microvesicles, and then other antigens can be bound to the antibody. Alternatively, antibodies can be immobilized onto a solid phase via protein A or G or the like.

The timing of antibody immobilization is not particularly limited and an antibody may be immobilized before, after, or simultaneously upon contact with a sample. An arbitrary solid phase may be used to immobilize the antibodies. Such solid phases include membranous, particulate, or fibrous carriers, which are made of glass; organic polymers such as polystyrene; and inorganic materials such as silica gel, alumina, and activated carbon. For example, the antibodies of the present invention may be immobilized onto the inner wall of a reaction container such as a plate, dish, and test tube, or to a bead.

Immunological methods for detecting or quantifying microvesicles using the antibodies of the present invention for detecting microvesicles include, but not limited to, for example, fluorescence antibody methods (see Monoclonal Antibodies: Principle and Practice, 3rd ed. (1996) Academic Press), ELISAs, RIAs, immunohistochemical staining such as immunocytological staining and immunohistological staining, (see, for example, the ABC method and CSA method; Monoclonal Antibodies: Principle and Practice, 3rd ed. (1996) Academic Press), Western blotting, and immunoprecipitation.

The term "average amount" as used herein is calculated by determining the levels or concentrations of CSE1L or phosphorylated CSE1L present in one or more samples and then calculates the average value of the levels. An average may be determined by summing a plurality of individual values and dividing by the number of values. The term "average amount of CSE1L in microvesicles" used herein refers to an average amount of CSE1L protein in microvesicles in one or more control biological fluid samples. The term "average amount of phosphorylated CSE1L in microvesicles" used herein refers to an average amount of phosphorylated CSE1L protein in microvesicles in one or more control biological fluid samples. The term "average amount of phosphorylated CSE1L in the control biological fluid samples" used herein refers to an average amount of phosphorylated CSE1L protein in one or more control biological fluid samples. "An increased amount" as used herein refers to a positive change in amount of the test sample as compared to the average amount of the control samples. An increase is typically at least 10%, or at least 20%, or 50%, or 100%, or at least 2-fold, or at least 5-fold, and can be as high as at least 10-fold or even 20-fold.

As used herein, the term "cutoff value" or "cut-off value" refers to a threshold value which distinguishes subjects suffering from a disease or condition from subjects who are not suffering from the disease or condition. Cutoff value is a statistically derived optimal number for using as a diagnostic tool wherein a mean and standard deviation (SD) of test values are calculated from a group of read-out values from a category of patients. When a patient's test value is less than this cutoff value the patient may be considered negative (i.e. without cancer) and when a value is greater than or equal to cutoff value then the patient is considered positive (i.e. with cancer).

A "pharmaceutical composition" as used herein, refers to the combination of one or more drug substances and one or more excipients.

As used herein, the term "pharmaceutical excipient, diluent or carrier" includes any of the standard pharmaceutical excipient, diluent or carrier, such as a phosphate buffered saline solution, water, emulsions such as an oil/water or water/oil emulsion, and various types of wetting agents. The term also encompasses any of the agents approved by a regulatory agency of the US Federal government or listed in the US Pharmacopeia for use in animals, including humans.

The term "treating" may be taken to mean prophylaxis of a specific disorder, disease or condition, alleviation of the symptoms associated with a specific disorder, disease or condition and/or prevention of the symptoms associated with a specific disorder, disease or condition.

As used herein, a "kit" refers to one or more items, including, but not limited to, compounds, compositions, combinations, instruments and devices, suitably packaged for use. Kits provided herein optionally contain instructions for use.

In addition, the "kit" may include instructional materials containing directions (i.e., protocols) for the practice of the methods of this invention. While the instructional materials typically comprise written or printed materials, they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), and the like. Such media may include links to Internet sites that provide such instructional materials.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described herein. As used herein, each of the terms has the meaning associated with it in this section.

It should be understood that this invention is not limited to the particular methodologies, protocols and reagents, described herein and as such may vary. The terminology used herein is for the purpose of describing particular embodiments only, and is not intended to limit the scope of the present invention, which is defined solely by the claims.

The CSE1L protein and its gene are known in the art. The DNA sequences of CSE1L gene (GenBank accession no. U33286) are shown below:

```
                                                                  SEQ ID NO: 1
   1 gtcgcgccat tttgccgggg tttgaatgtg aggcggagcg gcggcaggag cggatagtgc 61 cagctacggt ccgcggctgg ggttccctcc tccgtttctg tatcccacg  agatcctata 121 gcaatggaac tcagcgatgc aaatctgcaa acactaacag aatatttaaa gaaaacactt 181 gatcctgatc ctgccatccg acgtccagct gagaaatttc ttgaatctgt tgaaggaaat 241 cagaattatc cactgttgct tttgacatta ctggagaagt cccaggataa tgttatcaaa 301 gtatgtgctt cagtaacatt caaaaactat attaaaagga actggagaat tgttgaagat 361 gaaccaaaca aaatttgtga agccgatcga gtggccatta aagccaacat agtgcacttg 421 atgcttagca gcccagagca aattcagaag cagttaagtg atgcaattag cattattggc 481 agagaagatt tccacagaa  atggcctgac ttgctgacag aaatggtgaa tcgctttcag 541 agtggagatt tccatgttat taatggagtc ctccgtacag cacattcatt atttaaaaga 601 taccgtcatg aatttaagtc aaacgagtta tggactgaaa ttaagcttgt tctggatgcc 661 tttgctttgc ctttgactaa tcttttttaag gccactattg aactctgcag tacccatgca 721 aatgatgcct ctgccctgag gattctgttt tcttccctga tcctgatctc aaaattgttc 781 tatagtttaa acttttcagga tctccctgaa ttttgggaag gtaatatgga aacttggatg 841 aataatttcc atactctctt aacattggat aataagcttt tacaaactga tgatgaagag 901 gaagccggct tattggagct cttaaaatcc cagatttgtg ataatgccgc actctatgca 961 caaaagtacg atgaagaatt ccagcgatac ctgcctcgtt ttgttacagc catctggaat 1021 ttactagtta caacgggtca agaggttaaa tatgatttgt tggtaagtaa tgcaattcaa 1081 tttctggctt cagtttgtga gagacctcat tataagaatc tatttgagga ccagaacacg 1141 ctgacaagta tctgtgaaaa ggttattgtg cctaacatgg aatttagagc tgctgatgaa
```

-continued

```
1201 gaagcatttg aagataattc tgaggagtac ataaggagag atttggaagg atctgatatt
1261 gatactagac gcagggctgc ttgtgatctg gtacgaggat tatgcaagtt ttttgaggga
1321 cctgtgacag gaatcttctc tggttatgtt aattccatgc tgcaggaata cgcaaaaaat
1381 ccatctgtca actggaaaca caaagatgca gccatctacc tagtgacatc tttggcatca
1441 aaagcccaaa cacagaagca tggaattaca caagcaaatg aacttgtaaa cctaactgag
1501 ttctttgtga atcacatcct ccctgattta aaatcagcta atgtgaatga atttcctgtc
1561 cttaaagctg acggtatcaa atatattatg atttttagaa atcaagtgcc aaaagaacat
1621 cttttagtct cgattcctct cttgattaat catcttcaag ctggaagtat tgttgttcat
1681 acttacgcag ctcatgctct tgaacggctc tttactatgc gagggcctaa caatgccact
1741 ctctttacag ctgcagaaat cgcaccgttt gttgagattc tgctaacaaa ccttttcaaa
1801 gctctcacac ttcctggctc ttcagaaaat gaatatatta tgaaagctat catgagaagt
1861 ttttctctcc tacaagaagc cataatcccc tacatcccta ctctcatcac tcagcttaca
1921 cagaagctat tagctgttag taagaaccca agcaaacctc actttaatca ctacatgttt
1981 gaagcaatat gtttatccat aagaataact tgcaaagcta accctgctgc tgttgtaaat
2041 tttgaggagg ctttgttttt ggtgtttact gaaatcttac aaaatgatgt gcaagaattt
2101 attccatacg tctttcaagt gatgtctttg cttctggaaa cacacaaaaa tgacatcccg
2161 tcttcctata tggccttatt tcctcatctc cttcagccag tgctttggga agaacagga
2221 aatattcctg ctctagtgag gcttcttcaa gcattcttag aacgcggttc aaacacaata
2281 gcaagtgctg cagctgacaa aattcctggg ttactaggtg tctttcagaa gctgattgca
2341 tccaaagcaa atgaccacca aggtttttat cttctaaaca gtataataga gcacatgcct
2401 cctgaatcag ttgaccaata taggaaacaa atcttcattc tgctattcca gagacttcag
2461 aattccaaaa caaccaagtt tatcaagagt ttttagtct ttattaattt gtattgcata
2521 aaatatgggg cactagcact acaagaaata tttgatggta tacaaccaaa aatgtttgga
2581 atggttttgg aaaaaattat tattcctgaa attcagaagg tatctggaaa tgtagagaaa
2641 aagatctgtg cggttggcat aaccaactta ctaacgaat gtcccccaat gatggacact
2701 gagtatacca aactgtggac tccattatta cagtctttga ttggtctttt tgagttaccc
2761 gaagatgata ccattcctga tgaggaacat tttattgaca tagaagatac accaggatat
2821 cagactgcct tctcacagtt ggcatttgct gggaaaaaag agcatgatcc tgtaggtcaa
2881 atggtgaata cccccaaaat tcacctggca cagtcacttc acatgttgtc taccgcctgt
2941 ccaggaaggg ttccatcaat ggtgagcacc agcctgaatg cagaagcgct ccagtatctc
3001 caagggtacc ttcaggcagc cagtgtgaca ctgctttaaa ctgcattttt ctaatgggct
3061 aaacccagat ggtttcctag gaaatcacag gcttctgagc acagctgcat taaaacaaag
3121 gaagttttcc ttttgaactt gtcacga
```

The amino acid sequences of the CSE1L protein (Protein ID Accession No. AAC50367.1) are shown below:

SEQ ID NO: 2

MELSDANLQTLTEYLKKTLDPDPAIRRPAEKFLESVEGNQNYPL

LLLTLLEKSQDNVIKVCASVTFKNYIKRNWRIVEDEPNKICEADRVAIKANIVHLMLS

SPEQIQKQLSDAISIIGREDFPQKWPDLLTEMVNRFQSGDFHVINGVLRTAHSLFKRY

RHEFKSNELWTEIKLVLDAFALPLTNLFKATIELCSTHANDASALRILFSSLILISKL

-continued

```
FYSLNFQDLPEFWEGNMETWMNNFHTLLTLDNKLLQTDDEEEAGLLELLKSQICDNAA

LYAQKYDEEFQRYLPRFVTAIWNLLVTTGQEVKYDLLVSNAIQFLASVCERPHYKNLF

EDQNTLTSICEKVIVPNMEFRAADEEAFEDNSEEYIRRDLEGSDIDTRRRAACDLVRG

LCKFFEGPVTGIFSGYVNSMLQEYAKNPSVNWKHKDAAIYLVTSLASKAQTQKHGITQ

ANELVNLTEFFVNHILPDLKSANVNEFPVLKADGIKYIMIFRNQVPKEHLLVSIPLLI

NHLQAGSIVVHTYAAHALERLFTMRGPNNATLFTAAEIAPFVEILLTNLFKALTLPGS

SENEYIMKAIMRSFSLLQEAIIPYIPTLITQLTQKLLAVSKNPSKPHFNHYMFEAICL

SIRITCKANPAAVVNFEEALFLVFTEILQNDVQEFIPYVFQVMSLLLETHKNDIPSSY

MALFPHLLQPVLWERTGNIPALVRLLQAFLERGSNTIASAAADKIPGLLGVFQKLIAS

KANDHQGFYLLNSIIEHMPPESVDQYRKQIFILLFQRLQNSKTTKFIKSFLVFINLYC

IKYGALALQEIFDGIQPKMFGMVLEKIIIPEIQKVSGNVEKKICAVGITNLLTECPPM

MDTEYTKLWTPLLQSLIGLFELPEDDTIPDEEHFIDIEDTPGYQTAFSQLAFAGKKEH

DPVGQMVNNPKIHLAQSLHMLSTACPGRVPSMVSTSLNAEALQYLQGYLQAASVTLL
```

The amino acid sequence of the phosphopeptide used to produce antibodies specific to phosphorylated CSE1L (Protein ID Accession No. AAC50367.1) are shown below:

```
                                        SEQ ID NO: 3
LTpEYpLKKTLDPDPAC
(Tp denotes phosphothreonine and Yp denotes
phosphotyrosine)
```

EXAMPLE

Testing Materials and Methods
Antibodies

The antibodies used in the experiment were anti-p21/ras (EP1125Y) (Epitomics, Burlingame, Calif., USA); anti-CSE1L (3D8) and anti-MAPK1/MAPK3 (phospho T202/204, G15-B) (Abnova, Taipei, Taiwan); anti-CSE1L (24), anti-phosphotyrosine (PY20), and anti-phosphoserine/threonine (22A/pSer/Thr) (BD Pharmingen, San Diego, Calif., USA); anti-β-tubulin (D66) (Sigma, St. Louis, Mo., USA); anti-β-actin (Ab-5) and anti-GFP (Ab-1) (Lab Vision, Fremont, Calif., USA); anti-MMP-2 (H-76) and anti-phosphothreonine (H2) (Santa Cruz Biotechnology, Santa Cruz, Calif., USA); goat anti-mouse IgG (Jackson ImmunoResearch Laboratories, West Grove, Pa., USA); and goat anti-mouse (or anti-rabbit) IgG secondary antibodies coupled to Alexa Fluor 488 (or 568) (Molecular Probes, Eugene, Oreg., USA).

Plasmids v-H-Ras (pZIP-v-H-ras) expression vector carrying a neomycin selectable marker was kindly provided by Dr. Channing J. Der. Mammalian CSE1L expression vector, pcDNA-CSE1L, carrying a neomycin selectable marker was generated by inserting CSE1L cDNA (as an Apa I and Not I fragment from pGEM-CSE1L vector) into the Apa I and Not I sites of the pcDNA3.1 vector. The CSE1L shRNA plasmids (sc-29909-SH) designed to knockdown CSE1L expression, and the control shRNA plasmids (sc-108060) encode of a scrambled shRNA sequence that will not lead to the specific degradation of any cellular message were ordered from Santa Cruz Biotechnology (Santa Cruz). The CSE1L shRNA plasmids and the control shRNA plasmids carry the puromycin selectable marker.

Cells and DNA Transfections

B16F10 melanoma cells were obtained from the American Type Culture Collection (Manassas, Va., USA). Cells were cultured in Dulbecco's modified Eagle's medium supplemented with 10% heat-inactivated fetal bovine serum, 100 units/ml of penicillin, 100 mg/ml of streptomycin, and 2 mmol/L of glutamate at 37° C. under a humidified 5% $CO_2$ atmosphere. B16F10 cells were transfected with the control pZIP-NeoSV(X)1 empty vector plus control shRNA plasmids, pZIP-v-H-ras plus control shRNA plasmids, pcDNA-CSE1L plus control shRNA plasmids, and pZIP-v-H-ras plus CSE1L shRNA plasmids to obtain B16-dEV, B16-Ras, B16-CSE1L, and B16-Ras/anti-CSE1L cells, respectively, by using the Lipofectamine plus reagent (Invitrogen, Carlsbad, Calif., USA) according to the manufacturer's instructions. Transfected cells were selected with 1 mg/ml G418 for 3 weeks then with 1 μg/ml puromycin for 3 weeks. Multiple drug-resistant colonies (>50) were pooled together and amplified in mass culture. The transfected cells were maintained in media containing 200 μg/ml G418 and 0.2 μg/ml puromycin; for the experiments, cells were cultured in medium without G418 and puromycin.

Immunoblotting

Cells were washed with phosphate-buffered saline (PBS) and lysed in ice-cold radioimmunoprecipitation assay (RIPA) buffer [25 Mm Tris-HCl (pH 7.2), 0.1% SDS, 0.1% Triton X-100, 1% sodium deoxycholate, 150 mM NaCl, 1 mM EDTA, 1 mM sodium orthovanadate, 1 mM phenylmethylsulfonyl fluoride, 10 μg/ml aprotinin, 5 μg/ml leupeptin, 25 mM β-glycerophosphate, 5 mM sodium orthovanadate, and 5 mM sodium fluoride]. The protein concentrations were determined with a BCA protein assay kit (Pierce, Rockford, Ill., USA). Fifty micrograms of each protein sample was loaded onto SDS-polyacrylamide gel. Proteins were transferred to nitrocellulose membranes (Amersham Pharmacia, Buckinghamshire, UK). The membrane was blocked in blocking buffer [1% bovine serum albumin (BSA), 50 mM Tris-HCl (pH 7.6), 150 mM NaCl, and 0.1% Tween-20] at room temperature for 1 h. The blots were then incubated with primary antibodies at 4° C. overnight followed by incubation with secondary antibodies conjugated to horseradish peroxidase for 1 h. The levels of protein were detected by Forte Western HRP Substrate (Millipore Corp., Billerica, Mass., USA) according to the manufacturer's instructions.

For Immunoblotting with biotin-conjugated antibodies, the biotin-conjugated antibody was prepared by biotinylating anti-CSE1L antibodies using the Biotin Labeling Kit-NH2 kit according to the manufacturer's protocol (Dojindo Laboratories, Kumamoto, Japan). The Immunoblot was then reacted with horseradish peroxidase (HRP)-conjugated streptavidin and the levels of protein were detected by Forte Western HRP Substrate.

Immunofluorescence and Microvesicle Scoring

Cells grown on glass cover slides (12×12 mm) for 4 days were cytospun at 1000 rpm for 10 min. Cells were washed with PBS, fixed with 4% paraformaldehyde, permeabilized with methanol, and blocked with PBS containing 0.1% BSA. Samples were incubated with primary antibodies for 1 h. Samples were then washed three times with PBS and followed by incubating with secondary antibodies coupled to Alexa Fluor 488 (or 568) and examined with a inverted fluorescence microscope. For each experimental condition, cells that showed microvesicles at the surface were scored. Three hundred cells were observed for each experiment, and the data from three independent experiments are plotted. Standard deviation bars are shown.

Cell Proliferation Assay

Equal numbers of cells ($1 \times 10^4$ cells/dish) were seed on 100 mm culture dishes. The media were refreshed every three days. The cell numbers were countered every 24 h by trypan blue exclusion assays after cell seeding. For each time point, three plates of cells were counted, and each plate was only counted once.

Conditioned Medium

Cells were grown to subconfluence, washed with PBS, and changed to medium without fetal bovine serum. After incubation for 48 h, the conditioned medium was collected and the cell numbers were counted. To remove possible suspended cells or cell debris, medium was centrifuged at 10,000 rpm for 10 minutes, after which supernatant was harvested.

Preparation of Microvesicles

Microvesicles were prepared from conditioned media or sera by size exclusion chromatography and ultracentrifugation. Briefly, conditioned media or sera were applied to a Sepharose 2B column (Amersham Biosciences, NJ, USA) equilibrated with PBS. Fractions (1 ml) were collected, and the protein content was monitored by measuring absorbance at 280 nm. The void volume peak material, containing proteins of >50 million kDa, was then centrifuged at 105,000 g for 1 h at 4° C. The pellet contains microvesicles and was resuspended with 50 µl of PBS.

Immunoprecipitation

Cells grown on plastic dishes were washed with PBS and incubated in immunoprecipitation lysis buffer [10 mM Tris-HCl (pH 7.4), 10 mM EDTA, 0.4% deoxycholic acid, 0.5% Triton X-100, 1 mM phenylmethylsulfonyl fluoride, 10 µg/ml aprotinin, 5 µg/ml leupeptin, 25 mM β-glycerophosphate, 5 mM sodium orthovanadate, and 5 mM sodium fluoride] at 4° C. for 20 min. Cells were scraped and disrupted by pipetting. The cell lysate was cleared of insoluble materials by centrifugation at 12,000 g for 10 min at 4° C., and the protein concentrations were determined with a BCA protein assay kit (Pierce). Cell lysate (500 µg) were incubated with primary antibodies in immunoprecipitation buffer [50 mM Tris-HCl (pH 7.5) and 150 mM NaCl] at 4° C. for 3 h followed by a slurry of protein A/G plus agarose beads (Santa Cruz) and incubated for additional 2 h. The immunoprecipitates were washed with lysis buffer three times and then subjected to SDS-PAGE and immunoblotting with antibodies. Mouse anti-GFP antibodies were used in the control reactions.

For immunoprecipitation with serum samples, sera were incubated in PBS containing agarose-conjugated anti-phosphothreonine antibodies (H2) (Santa Cruz) at 4° C. overnight with slow rotation. The immunoprecipitates were washed with immunoprecipitation lysis buffer three times and then subjected to SDS-PAGE and immunoblotting with anti-CSE1L antibodies. Control immunoprecipitation was performed using agarose-conjugated normal mouse IgG (Santa Cruz).

Production of GST-CSE1L Fusion Protein

GST-CSE1L fusion protein was produced using wheat germ cell-free protein synthesis system according to the method described by ENDEXT technology protocol (Cell-Free Sciences, Yokohama, Japan). Briefly, the open reading frame of CSE1L in pcDNA-CSE1L vector was cut with restriction enzymes and was subcloned into the wheat germ expression vector pPEU-E01-MCS (CellFree Sciences). Transcription of CSE1L mRNA was performed by adding 2 micrograms of the subcloned plasmid to a tube containing the transcription premix solution (CellFree Sciences). The mixture was incubated at 37° C. for 6 h for transcription reaction. Ten microliters of the mRNA mixture was added into 10 µL of wheat germ extract solution (WEPRO 3240, CellFree Sciences) for translation reaction. The translation mixture (20 µl) was transferred to the bottom of the well containing SUB-AMIX (CellFree Sciences) to form bilayer with the translation mixture in the lower layer. After incubated at 26° C. for 16 h, the mixture is used for purify of GST-CSE1L fusion protein. GST-CSE1L fusion proteins were purified using glutathione-Sepharose 4B beads and Bulk GST Purification Modules (Amersham Pharmacia). The purified GST-CSE1L fusion protein was cleaved with thrombin and GST was removed by using Amicon Ultra-4 Centrifugal Filter Units (Millipore, Billerica, Mass., USA).

Tissue Microarrays and Immunohistochemistry

Tissue cores from cancer tissue and tissue core from non-cancer tissues in each paraffin block was longitudinally cut and arranged into new paraffin blocks using a manual method of BiosynMatric Handmade Kit (Formosa Transcrip, Kaohsiung, Taiwan) to generate tissue microarrays. Tissue sections (4-µm) were stained with hematoxylin and eosin to confirm the presence of morphologically representative areas of the original cancers.

Immunohistochemistry was performed by using a 50-fold dilution of anti-CSE1L antibodies (clone 3D8) or anti-MAPK1/MAPK3 (phospho T202/204) antibodies. Immunohistochemical detection was carried out by using a labeled streptavidin-biotin method with the Histostain kit (Zymed, San Francisco, Calif., USA) according to the manufacturer's instructions. Sections were developed with diaminobenzidine, washed with distilled water, and counterstained with Mayer's hematoxylin.

Matrigel-Based Invasion Assay

The Matrigel-based invasion assay was done by using Matrigel (BD Biosciences) and 8 µm pore-sized polyvinylpyrrolidone-free polycarbonate filters (Costar, Cambridge, Mass., USA). The filters were coated with Matrigel (1:10 in DMEM) at 4° C. for overnight and 37° C. for additional 2 h. The filters were washed 3 times with DMEM and were placed in the microchemotaxis chambers. The cells were treated with 0.1% trypsin-EDTA, re-suspended in DMEM media containing 10% FBS and then washed with serum-free DMEM media. Cells ($3 \times 10^5$) were suspended in DMEM (200 µl) and placed in the upper compartment of the chemotaxis chambers. Culture medium (300 µl) containing 20% FBS was placed in the lower compartment of the chemotaxis chamber to serve as a source of chemoattractants. After being incubated in the culture incubator for 12 h, the cells on the upper surface of the filter were completely wiped away with a cotton swab. The cells on the lower surface of the filter were fixed in methanol, stained with Liu's A and Liu's B reagents, and then counted under a microscope. Cells invaded to the microchemotaxis chambers were also counted. The assays were repeated three times, and each assay consisted of four replicate of filters for each cell line. For each replicate, the tumor cells in 10 randomly selected fields were determined, and the counts were averaged.

Immunogold Electron Microscopy

Cells were washed with PBS and fixed in a mixture of 0.5% glutaraldehyde and 2% paraformaldehyde in Hepes buffer (pH 6.8) for 15 min and then in 2% paraformaldehyde in Hepes buffer (pH 6.8) at 4° C. for 14 days. Samples were dehydrated with 80% ethanol and infiltrated with increasing concentrations of Lowicryl HM20 resin (Polysciences, Tokyo, Japan). Polymerization of Lowicryl HM20 was performed by UV irradiation (wave-length peak at 360 nm) for 24 h. Ultrathin sections were cut and then mounted on nickel grids coated with 2% Neoprene (Ohken, Tokyo, Japan). After being sunk in 100% ethanol for 3 min, samples were immersed in 0.01 M EDTA (pH 7.2) at 65° C. for 24 h. The samples were washed with PBS three times (5 min/wash) and blocked with PBS containing 1% BSA and 0.1% Tween-20 for 15 min. The samples were incubated with a mixtures of primary antibodies diluted in PBS (1:30) for 1 h, washed with PBS three times (5 min/wash), reacted with 18-nm (or 12-nm) gold-labeled secondary antibodies, followed by washing with PBS three times (5 min/wash). The samples were stained with uranyl acetate and were examined on a Hitachi H-7000 transmission electron microscope (Hitachi, Tokyo, Japan).

Gelatin Zymography Assay

Microvesicles harvested from cell number-standardized conditioned media were resolved using 10% SDS-PAGE containing 1 mg/ml gelatin. The gel was washed twice with 2.5% Triton X-100 for 30 min to remove SDS, and subsequently incubated in buffer containing 50 mM Tris-HCl (pH 7.6), 200 mM NaCl, and 10 mM $CaCl_2$ at 37° C. for 24 h. The gel was stained with Comassie blue R-250 (0.125% Comassie blue R-250, 50% methanol, 10% acetic acid) for 30 min and destained with destaining solution (20% methanol, 10% acetic acid, 70% $ddH_2O$) until the clear bands were visualized.

Animal Metastasis Experiment

Male C57BL/6 mice ages between 6-7 (N=18) and 14-15 (N=26) weeks old (National Laboratory Animal Center, Taipei, Taiwan) were housed in an animal holding room under standard conditions (22° C.; 50% humidity; 12-hours light/dark cycle). The experiments included 4 groups (i.e. mice injected with B16-dEV, B16-CSE1L, B16-Ras, and B16-Ras/anti-CSE1L cells), and mice with different age were evenly distributed in the four groups. Each mouse was injected with viable cells ($3 \times 10^4$ cells in 100 µl PBS/mouse) in the tail vein. The experiment included eleven, fourteen, eight, and eleven mice injected with B16-dEV, B16-CSE1L, B16-Ras, and B16-Ras/anti-CSE1L cells, respectively. Three weeks after injection, the mice were sacrificed and necropsied. The numbers of tumors in lungs were counted by macrography and micrography. Mouse care and experimental procedures were performed following the guideline of the Animal Care Committee of Academia Sinica, Taiwan. There were 3, 10, 4, and 1 mice died three weeks after injected with B16-dEV, B16-CSE1L, B16-Ras, and B16-Ras/anti-CSE1L cells, respectively, and thus were excluded from the statistics. There were 1, 1, 0, and 3 mice injected with B16-dEV, B16-CSE1L, B16-Ras, and B16-Ras/anti-CSE1L cells, respectively, that did not grow tumor in the lungs, and thus were also excluded from the statistics.

Patients and Tumor Samples

Colorectal cancer samples were obtained from 115 consecutive patients who had recently been given a diagnosis at Changhua Christian Hospital, Taiwan at the time of diagnosis with informed consent using IRB-approved guidelines and had not yet been treated. All participants had the study explained to them and gave informed consent by using institutional review board-approved guidelines before any participation. The tumors were graded and categorized according to the sixth edition of the American Joint Committee on Cancer, Cancer Staging Manual. Control health donor serum samples were obtained from 60 healthy individuals (mean age, 61.0±8.7 years; range, 22-71 years). Serum samples were collected by allowing blood to sit at room temperature for a minimum of 30 min to allow clots to form. To remove any possible suspended cells or cell debris in serum, samples were centrifuged at 10,000 rpm for 10 min, after which supernatants were harvested and stored at −80° C. Baseline characteristics of the patients are shown in Table (Tables 1).

TABLE 1

Baseline characteristics of the colorectal cancer patients

| Clinicopathological parameter | Stage I (n = 13) | Stage II (n = 43) | Stage III (n = 43) | Stage IV (n = 16) |
|---|---|---|---|---|
| Mean age (range), year[a] | 66.0 ± 11.5, 42-84 | 65.4 ± 10.0, 40-93 | 60.3 ± 15.2, 28-92 | 71.1 ± 11.2, 46-87 |
| Sex | | | | |
| Male | 7 | 27 | 27 | 7 |
| Female | 6 | 16 | 16 | 9 |
| Tumor grade[b] | | | | |
| Grade 1 | 0 | 0 | 2 | 2 |
| Grade 2 | 13 | 41 | 39 | 14 |
| Grade 3 | 0 | 1 | 3 | 0 |
| Lymph node (N[c]) and distant metastasis (M[d]) | | | | |
| N0M0 | 13 | 43 | 0 | 0 |
| N1M0 | 0 | 0 | 23 | 0 |
| N2M0 | 0 | 0 | 20 | 0 |
| N0M1 | 0 | 0 | 0 | 1 |
| N1M1 | 0 | 0 | 0 | 15 |
| N2M1 | 0 | 0 | 0 | 0 |

[a]Mean ± SD.
[b]Grade 1: well differentiation, Grade 2: moderate differentiation, Grade 3: poor differentiation.
[c]N0: no regional lymph node metastasis, N1: metastasis in 1-3 regional lymph nodes, N2: metastasis in ≧4 regional lymph nodes,
[d]M0: no distant metastasis, M1: distant metastasis.

In Vivo Tumor Imaging

Anti-CSE1L antibodies (clone 24) and anti-mouse IgG were conjugated with quantum dots by using a Qdot 800 Antibody Conjugation Kit (Invitrogen) according to the manufacturer's instructions. Briefly, Qdots are activated with N-Succinimidyl 4-(N-maleimidomethyl)cyclohexane-1-carboxylate (SMCC) and the antibodies were reduced by dithiothreitol. The reduced antibodies were covalently coupled with activated Qdots and the conjugation reactions were quenched with β-mercaptoethanol. Conjugates are concentrated by ultrafiltration and purified by size exclusion chromatography. The concentrations of conjugates were determined with a spectrofluorometer.

Male C57BL/6 mice ages between 6-7 weeks were injected with viable B16-CSE1L cells ($3 \times 10^4$ cells in 100 µl PBS/ mouse) in the dorsal skin. Three weeks after tumor inoculation, mice bearing tumor were injected with quantum dots-conjugated anti-CSE1L antibodies or quantum dots-conjugated anti-mouse IgG (500 pmole in 100 μl PBS/mouse) into the tail vein. Mice were imaged using a Xenogen IVIS 200 imaging system (Excitation: 525/50 nm; Emission: 832/65 nm) at 0, 1 and 4 h post-injection. The NIR fluorescence images were acquired on a camera.

Production of Antibodies Specific to phospho-CSE1L

Phosphopeptide, LT$^p$EY$^p$LKKTLDPDPAC (SEQ ID NO: 3) (T$^p$ denotes phosphothreonine and Y$^p$ denotes phosphotyrosine), and nonphosphopeptide, LTEYLKKTLDPDPAC (SEQ ID NO: 3), were synthesized using the solid phase method. The phosphorylated peptides were conjugated through the N-terminal cysteine thiol to keyhole limpet haemocyanin (KLH). New Zealand rabbit was immunized five times with the peptides. The immune serum was collected a week after the last immunization. The IgG fractions were purified using a protein G column (Amersham Pharmacia Biotech, Uppsala, Sweden). The antibodies are purified by the phosphorylated peptide affinity column and then with non-phosphopeptide cross-adsorption to remove non-phospho-specific antibodies. The titer and the specificity of the antibodies were tested by ELISA and immunoblotting.

Dot Blots

Equal amount of purified microvesicle suspension (5 μl) were applied to nitrocellulose membranes (Amersham Pharmacia) with a 96-well dot-blot manifold apparatus (BRL, Bethesda, Md., USA). The membrane was blocked in blocking buffer [1% bovine serum albumin (BSA), 50 mM Tris-HCl (pH 7.6), 150 mM NaCl, and 0.1% Tween-20] at room temperature for 1 h. The blots were then incubated with primary antibodies at 4° C. overnight followed by incubation with secondary antibodies conjugated to horseradish peroxidase for 1 h. The levels of protein were detected by Forte Western HRP Substrate (Millipore) according to the manufacturer's instructions.

ELISA

Serum samples were plated in duplicates using 96-well Nunc Immunoplate MaxiSorb plates (Nunc, Roskilde, Denmark) at 4° C. overnight. Samples were aspirated and blocked in PBS containing 1% BSA. The blocking buffer was removed and then washed with PBST (0.05% Tween-20 in PBS). Wells were incubated with biotin-conjugated anti-phspho-CSE1L antibodies or biotin-conjugated anti-CSE1L antibodies for 1 h. The biotin-conjugated antibodies were prepared by biotinylating the antibodies using the Biotin Labeling Kit-NH$_2$ (Dojindo Laboratories, Kumamoto, Japan). Wells were then washed with PBST and reacted with streptavidin-conjugated horseradish peroxidase (R&D Systems, Minneapolis, Minn., USA), followed by incubation with substrate reagent (R&D Systems). For calibration, three blank wells containing PBS were used as the background value, and three blank wells containing PBS but did react with all other ELISA reagents were used as control wells. The absorbance at 450 nm was measured within 30 min with a Thermo Multiskan EX Microplate Photometer (Thermo Fisher Scientific, Waltham, Mass., USA). OD values of sample wells that were higher than the highest OD value of the control wells were considered CSE1L-positive or phspho-CSE1-positive.

Statistical Analysis

Data were analyzed by using the SPSS 14.0 statistic software. Statistical differences were analyzed by two-tailed Fisher's exact test. An α-level of ≦0.01 was considered statistically significant.

EXAMPLES

Example 1

Establishment of Cells Stably Transfected with v-H-ras, CSE1L, and v-H-ras Plus CSE1L shRNA Expressing Plasmids B16F10 melanoma cells were stably transfected with pZIP-v-H-ras, a retroviral expression vector carrying the v-H-ras coding region to established B16-Ras cells; pcDNA-CSE1L, a viral expression vector carrying the human CSE1L coding region to obtain B16-CSE1L cells; pZIP-v-H-ras plus CSE1L shRNA plasmids to obtain B16-Ras/anti-CSE1L cells. For control, B16-Ras cells and B16-CSE1L cells were also stably transfected with the control shRNA plasmids (pshEV) encode of a scrambled shRNA sequence that will not lead to the specific degradation of any cellular message; B16F10 cells were also stably transfected with the control vectors pshEV and pZIP-NeoSV(X)1 to obtain B16-dEV cells. The results of immunoblotting showed Ras levels were increased in B16-Ras and B16-Ras/anti-CSE1L cells; CSE1L levels were increased in B16-CSE1L cells and were decreased in B16-Ras/anti-CSE1L cells (FIG. 1).

FIG. 1 shows the immunoblot analyses of the levels of Ras and CSE1L in B16-dEV, B16-Ras cells, B16-CSE1L, and B16-Ras/anti-CSE1L cells. The levels of Ras and CSE1L in cell lysates prepared from B16F10 melanoma cells stably transfected with control empty vector, v-H-ras, CSE1L, and v-H-ras plus CSE1L shRNA expressing plasmids, i.e. the B16-dEV, B16-Ras cells, B16-CSE1L, and B16-Ras/anti-CSE1L cells, respectively as indicated were analyzed by immunoblot with anti-CSE1L and anti-Ras antibodies. β-Actin levels were assayed as a control.

Example 2 v-H-ras Induces Microvesicle Generation Of Tumor Cells

The ras oncogene is a key mediator of cell transformation and is present in a wide variety of human cancer; ERK is activated in response to a variety of extracellular stimuli and oncogenic products such as Ras and the ErbB proto-oncogene family, the important targets for molecularly-targeted therapy (Roberts et al. 2007). Microscopic examination showed the surfaces B16-Ras cells were decorated with many bubble-like microvesicles and this was not observed in the surfaces of B16F10 cells and B16-dEV control cells (FIG. 2A). Formations of exocytotic vesicles are often coupled with pseudopodia or protrusion extension (Bianco et al. 2005). Presence of developing microvesicles was observed at the base of pseudopodia or the cytoplasm of B16-Ras cells (FIG. 2B). Shedding microvesicles are enriched with metalloproteinase (Taraboletti et al. 2002). Matrix metalloproteinase-2 (MMP-2) was localized in microvesicles in B16-Ras cells (FIG. 2C). v-H-ras transfection increased levels of microvesicular MMP-2 and PD98059, a potential ERK activity inhibitor, treatment attenuated v-H-ras-induced increase in MMP-2 in microvesicles (FIG. 2D). DAPI (4',6-diamidino-2-phenylindole) staining showed no signs of apoptotic chromatin condensation/fragmentation in the cells. Thus, the presence of microvesicles in B16-Ras cell membrane was related with microvesicle generation and ERK was involved in microvesicle generation induced by v-H-ras.

Figure 2:
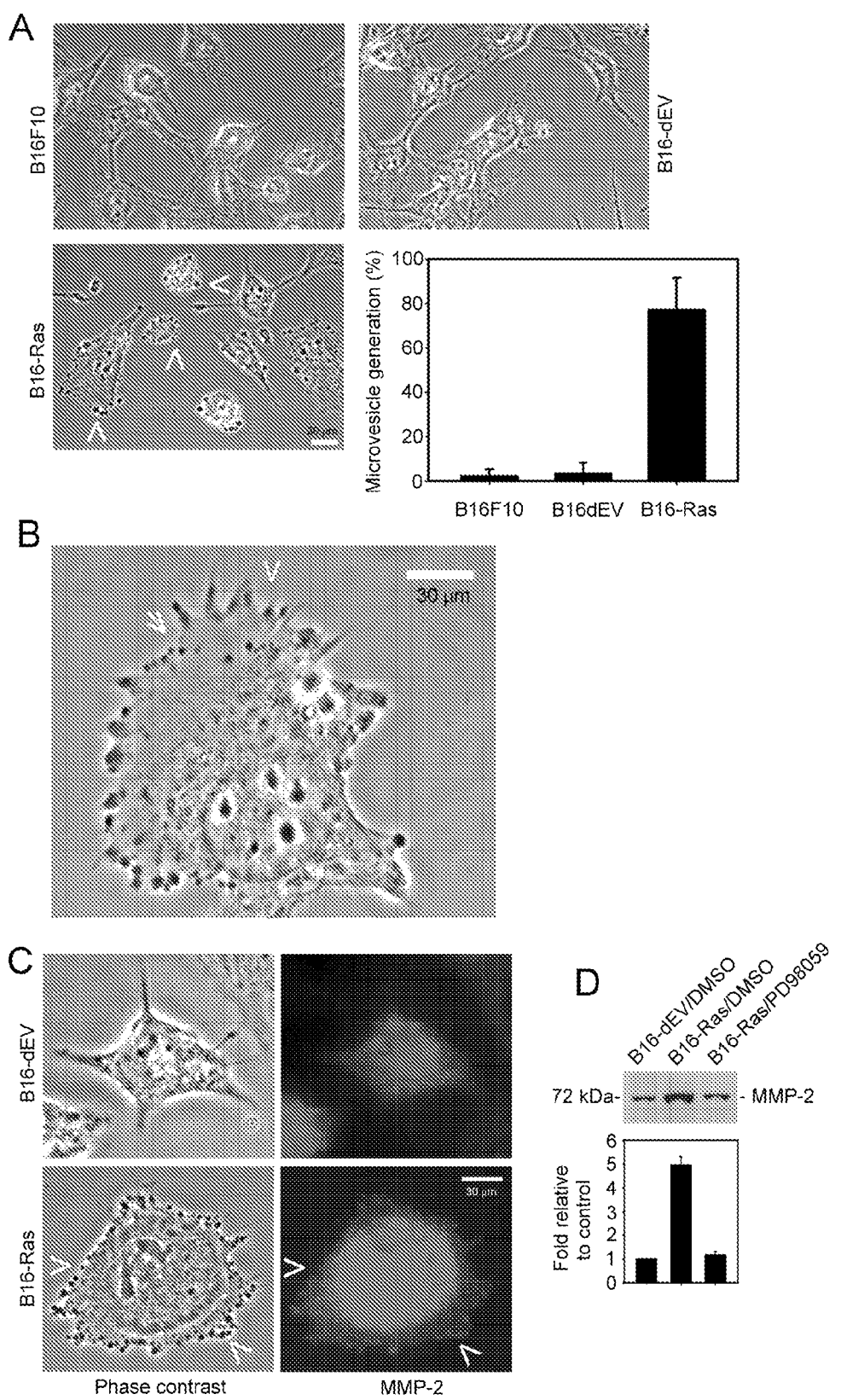
FIG. 2 refers to v-H-ras oncogene transfection induces microvesicle biogenesis in cells. (A) Inverted micrograph of B16F10, B16-dEV, and B16-Ras cells grown on glass cover slides for 4 days. (B) Presence of developing microvesicles at the base of pseudopodia (arrowhead) and cell membrane (arrow) of B16-Ras cells. (C) Immunofluorescence with anti-MMP-2 antibodies showed MMP-2 was localized in microvesicles (arrowhead) in B16-Ras cells. (D) Levels of microvesicular MMP-2 in microvesicles harvested from cell number-standardized conditioned media of serum-starved B16-dEV and B16-Ras cells treated with DMSO or 50 µM PD98059 for 48 h.

FIG. 2 shows v-H-ras induces microvesicle biogenesis in cells. (A) Inverted micrograph of B16F10, B16-dEV, and B16-Ras cells grown on glass cover slides for 4 days. (B) Presence of developing microvesicles at the base of pseudopodia (arrowhead) and cell membrane (arrow) of B16-Ras cells. (C) Immunofluorescence with anti-MMP-2 antibodies showed MMP-2 was localized in microvesicles (arrowhead) in B16-Ras cells. (D) Levels of microvesicular MMP-2 in microvesicles harvested from cell number-standardized conditioned media of serum-starved B16-dEV and B16-Ras cells treated with DMSO or 50 µM PD98059 for 48 h.

Example 3 v-H-ras Transfection Increases CSE1L Secretion

Figure 3:
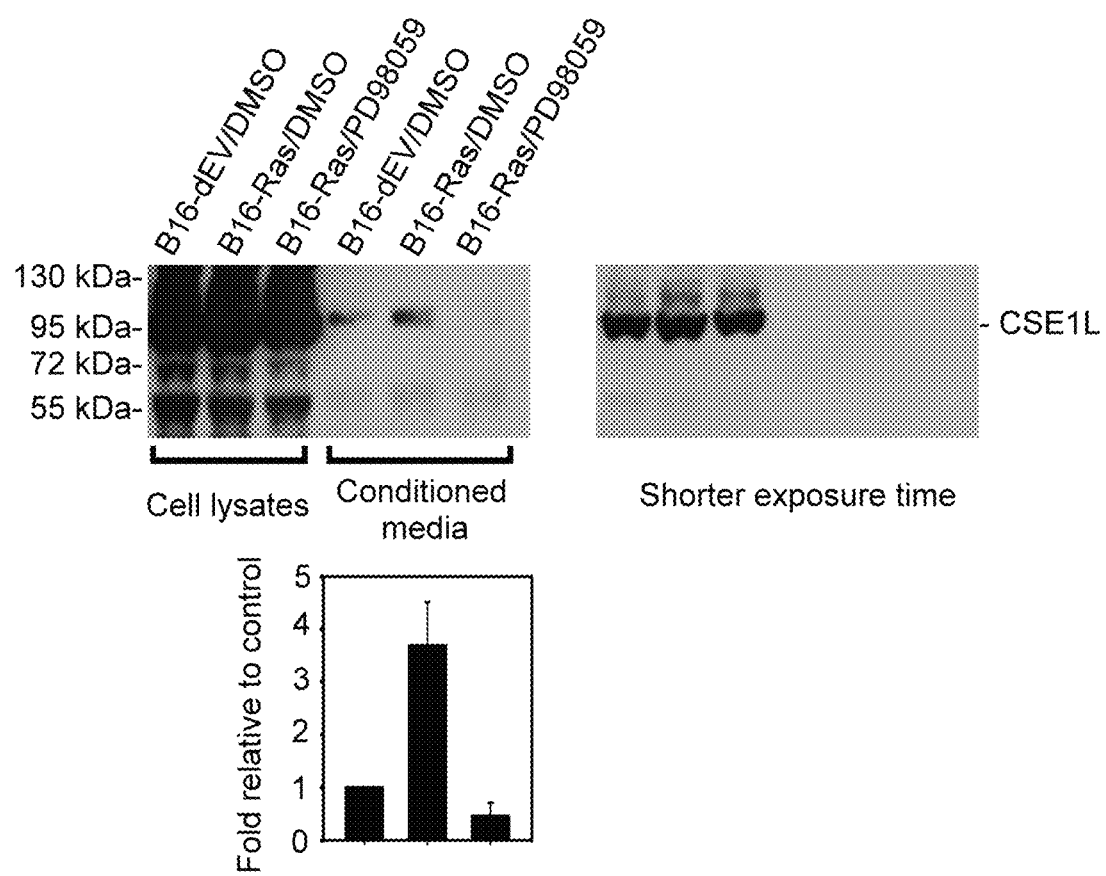
FIG. 3 refers to v-H-ras transfection increases CSE1L secretion. Levels of CSE1L in the cell lysates and the cell number-standardized conditioned media harvested from serum-starved B16-dEV and B16-Ras cells treated with DMSO or 50 µM PD98059 for 24 h were analyzed by immunoblotting with biotin-conjugated anti-CSE1L antibodies and horseradish peroxidase (HRP)-conjugated streptavidin.

The results of immunoblotting showed v-H-ras transfection increased CSE1L secretion, and PD98059 treatment attenuated v-H-ras-induced increase in CSE1L secretion of B16F10 cells (FIG. 3). v-H-ras transfection and PD98059 treatment did not obviously affect CSE1L expression in cells (FIG. 3). Thus, v-H-ras transfection stimulated CSE1L secretion and this was related with ERK activity.

FIG. 3 shows the levels of CSE1L in the cell lysates and the cell number-standardized conditioned media harvested from serum-starved B16-dEV and B16-Ras cells treated with DMSO or 50 µM PD98059 for 24 h analyzed by immunoblotting with biotin-conjugated anti-CSE1L antibodies and horseradish peroxidase (HRP)-conjugated streptavidin.

Example 4

CSE1L is a Serine/Threonine and Tyrosine Phosphorylated Protein

Figure 4:
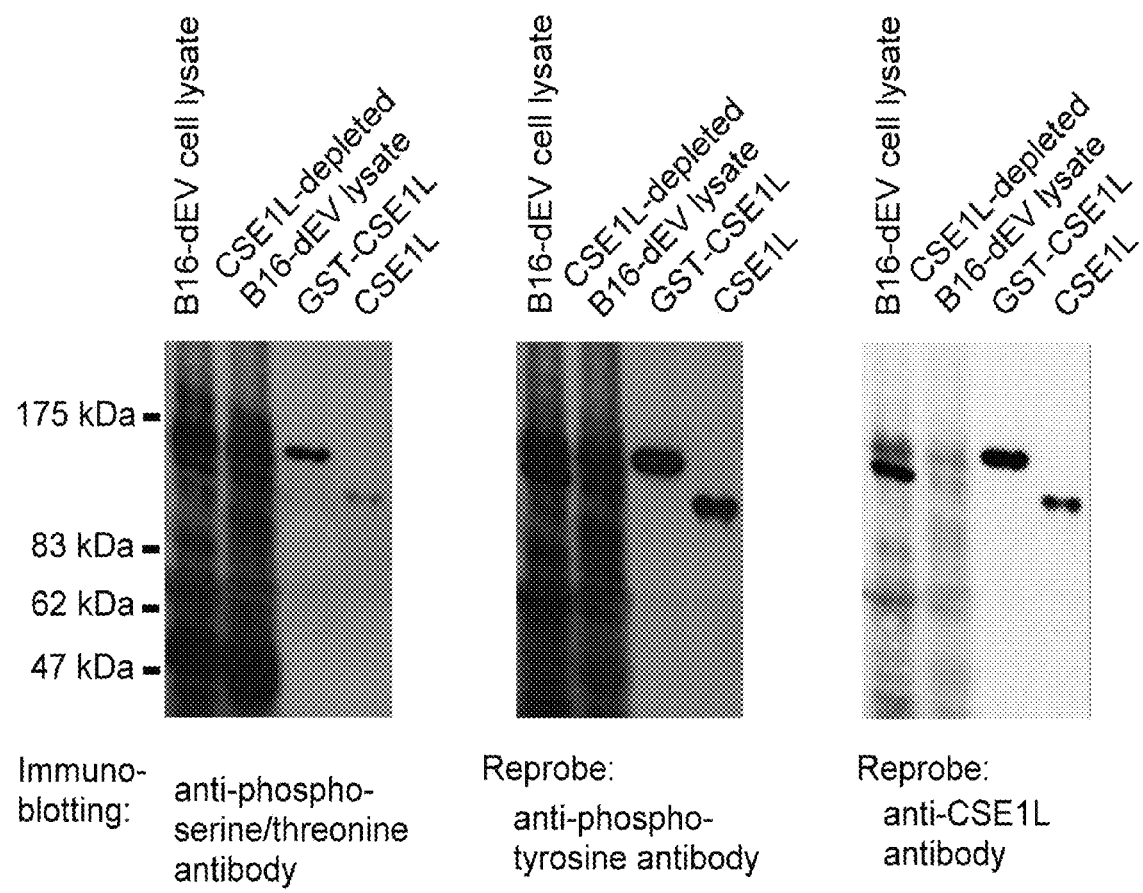
FIG. 4 refers to CSE1L is a phosphorylated protein. Immunoblot analyses of CSE1L phosphorylation with synthesized GST-CSE1L protein produced by wheat germ cell-free protein synthesis system and antibodies against phosphoserine/threonine, phosphotyrosine, and CSE1L. The CSE1L protein was obtained by cleavage of GST-CSE1L fusion protein with thrombin. Lane 2 is a CSE1L-depleted cell lysate made by harvesting the supernatant of B16-dEV cell lysate that treated with anti-CSE1L antibodies and A/G plus-agarose.

GST-CSE1L fusion protein was synthesized with the wheat germ cell-free protein synthesis system. Immunoblotting showed synthesized CSE1L protein reacted with anti-phosphoserine/threonine and anti-phosphotyrosine antibodies (FIG. 4). Therefore, CSE1L is a serine/threonine and tyrosine phosphorylated protein.

FIG. 4 shows the immunoblot analyses of CSE1L phosphorylation with synthesized GST-CSE1L protein produced by wheat germ cell-free protein synthesis system and antibodies against phosphoserine/threonine, phosphotyrosine, and CSE1L. The CSE1L protein was obtained by cleavage of GST-CSE1L fusion protein with thrombin. Lane 2 is a CSE1L-depleted cell lysate made by harvesting the supernatant of B16-dEV cell lysate that treated with anti-CSE1L antibodies and A/G plus-agarose.

Example 5 v-H-ras Transfection Increased CSE1L Phosphorylation and Phosphorylated CSE1L is Present in Cancer Sera CSE1L proteins in cell lysates purified from B16-dEV cells, B16-Ras cells, and PD98059-treated B16-Ras cells were immunoprecipitated with anti-CSE1L antibodies. The immunoprecipitates were immunoblotted with HRP (horseradish peroxidase)-conjugated anti-phosphothreonine antibodies. The results showed that v-H-ras transfection in B16F10 cells resulted in increased threonine phosphorylation of CSE1L, and PD98059 treatment inhibited v-H-ras-increased threonine phosphorylation in CSE1L (FIG. 5A). Thus, CSE1L is a phosphorylated protein and it can be phosphorylated by Ras-ERK signaling. CSE1L proteins in cell number-standardized conditioned media harvested from serum-starved B16-dEV, B16-Ras, and PD98059-treated B16-Ras cells were immunoprecipitated with anti-CSE1L antibodies. The immunoprecipitates were immunoblotted with HRP-conjugated anti-phosphothreonine antibodies. The results showed that v-H-ras transfection in B16F10 cells increased the secretion of threonine phosphorylated CSE1L, and PD98059 treatment inhibited v-H-ras-increased secretion of threonine phosphorylated CSE1L into the conditioned media form B16-Ras cells (FIG. 5B).

The level of threonine phosphorylated CSE1L in the sera of patients with colorectal cancer and healthy donors were analyzed. Serum threonine phosphorylated protein in sera harvested from the colorectal cancer patients (N=36) or healthy donors (N=36) were immunoprecipitated with agarose-conjugated anti-phosphothreonine antibodies. The immunoprecipitates were immunoblotted with anti-CSE1L antibodies. The results showed the presence of threonine phosphorylated CSE1L in the immunoprecipitates from cancer sera samples but not from normal sera samples (FIG. 5C). Although the serum CSE1L level was higher in cancer sample than in healthy donor sample; the difference was not as significant as that seen in the assay of threonine phosphorylated CSE1L (FIG. 5D).

Figure 5:
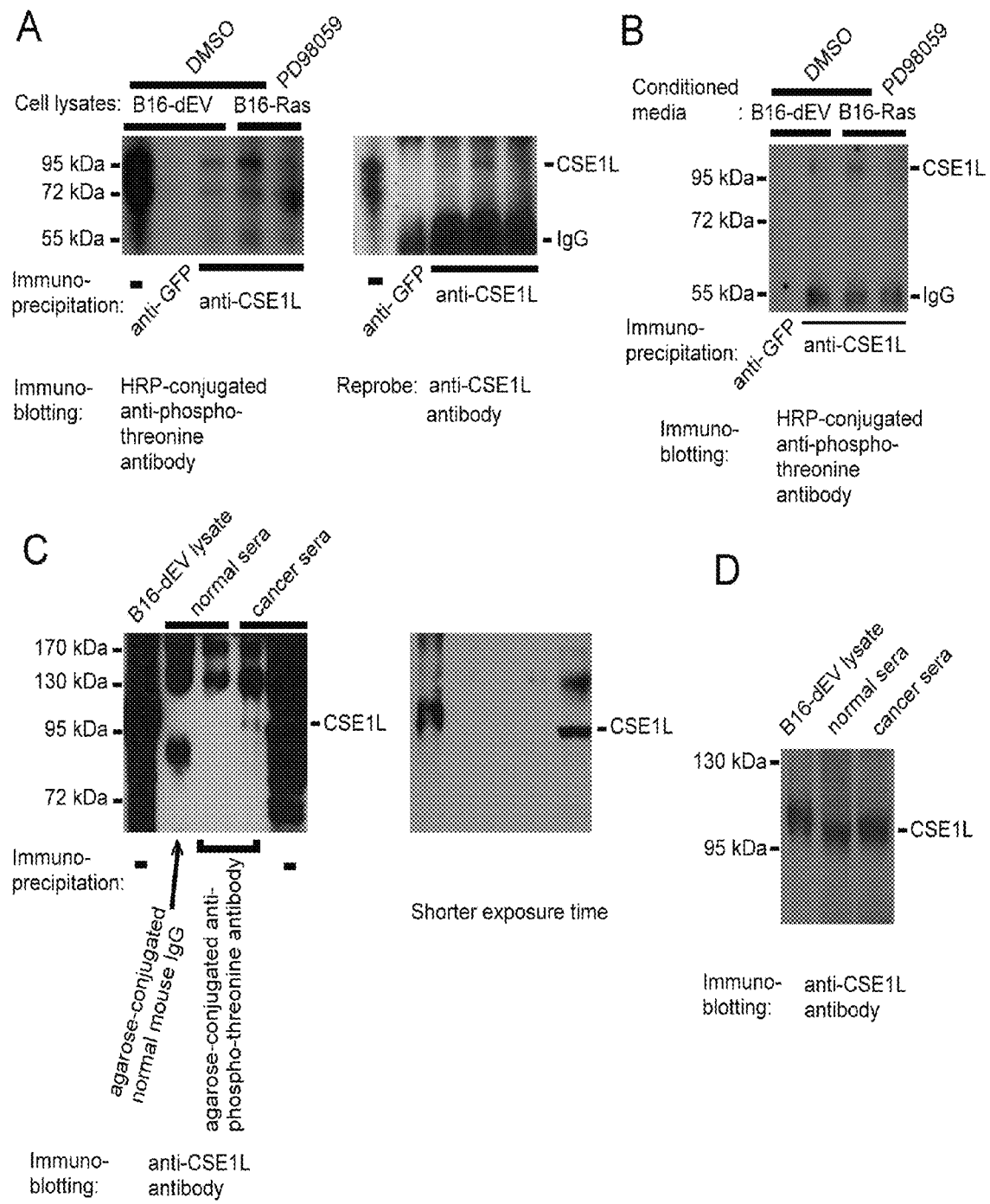
FIG. 5 refers to v-H-ras transfection increased CSE1L phosphorylation and phosphorylated CSE1L is present in cancer sera. (A) Levels of cellular threonine phosphorylated CSE1L in B16-dEV cells and B16-Ras cells treated with DMSO or 50 µM PD98059 for 24 h were analyzed by immunoprecipitation with anti-CSE1L antibodies and immunoblotting with HRP-conjugated anti-phosphothreonine antibodies. The immunoblot was reprobed with anti-CSE1L antibodies. Control immunoprecipitation was performed using mouse anti-GFP antibodies. (B) Levels of secretory threonine phosphorylated CSE1L in cell number-standardized conditioned media harvested from serum-starved B16-dEV cells and B16-Ras cells treated with DMSO or 50 µM PD98059 for 24 h were analyzed by immunoprecipitation with anti-CSE1L antibodies and immunoblotting with HRP-conjugated anti-phosphothreonine antibodies. (C) Serum threonine phosphorylated CSE1L analyzed by immunoprecipitation of a pool of sera from colorectal cancer patients (36 patients, each 10 µl) or 36 healthy donors (each 10 µl) with agarose-conjugated anti-phosphothreonine antibodies and immunoblotting with anti-CSE1L antibodies. Control immunoprecipitation was performed using agarose-conjugated normal mouse IgG. (D) Levels of CSE1L in the pool of cancer sera and normal sera were analyzed by immunoblotting.

FIG. 5 shows v-H-ras transfection increased CSE1L phosphorylation and phosphorylated CSE1L is present in cancer sera. (A) Levels of cellular threonine phosphorylated CSE1L in B16-dEV cells and B16-Ras cells treated with DMSO or 50 µM PD98059 for 24 h were analyzed by immunoprecipitation with anti-CSE1L antibodies and immunoblotting with HRP-conjugated anti-phosphothreonine antibodies. The immunoblot was reprobed with anti-CSE1L antibodies. Control immunoprecipitation was performed using mouse anti-GFP antibodies. (B) Levels of secretory threonine phosphorylated CSE1L in cell number-standardized conditioned media harvested from serum-starved B16-dEV cells and B16-Ras cells treated with DMSO or 50 µM PD98059 for 24 h were analyzed by immunoprecipitation with anti-CSE1L antibodies and immunoblotting with HRP-conjugated anti-phosphothreonine antibodies. (C) Serum threonine phosphorylated CSE1L analyzed by immunoprecipitation of a pool of sera from colorectal cancer patients (36 patients, each 10 µl) or 36 healthy donors (each 10 µl) with agarose-conjugated anti-phosphothreonine antibodies and immunoblotting with anti-CSE1L antibodies. Control immunoprecipitation was performed using agarose-conjugated normal mouse IgG. (D) The levels of CSE1L in the pool of cancer sera and normal sera were analyzed by immunoblotting with anti-CSE1L antibodies (clone 24).

Example 6

High Expression of phospho-ERK and CSE1L in Colorectal Cancer and Coincidence in the Relative Staining Intensity of phospho-ERK with CSE1L in Tumors The results of tissue microarray immunohistochemistry consists of 115 colorectal cancer specimens showed heavy staining of phospho-ERK (100%, 115/115) and CSE1L (99.1%, 114/115) in the colorectal cancer specimens (FIG. 6A). The normal tissue only showed weak phospho-ERK and CSE1L staining (FIG. 6A). Noteworthily, a coincidence of the relative staining intensity of CSE1L with phospho-ERK in tumors was observed in 97.4% (112/115) of the specimens, indicating that there is a close relationship between CSE1L and ERK in the progression of colorectal cancer (FIG. 6B).

Figure 6:
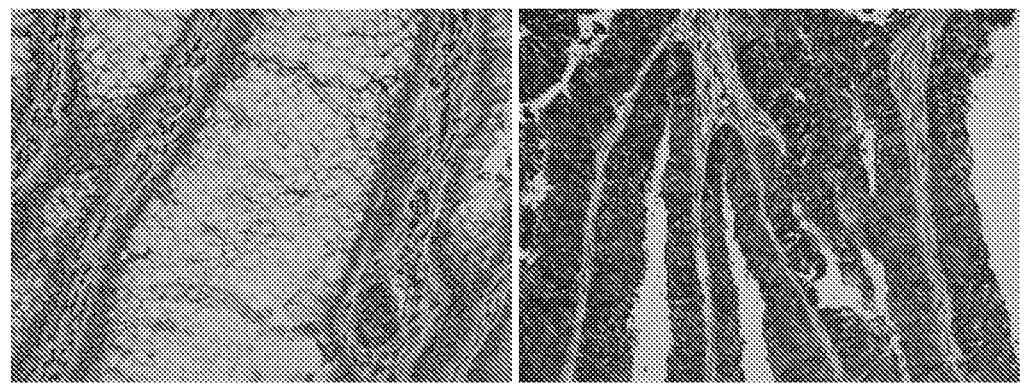
FIG. 6 refers to high expression of phospho-ERK and CSE1L in colorectal cancer and coincidence in the relative staining intensity of phospho-ERK with CSE1L in tumors. (A) Expression of phospho-ERK and CSE1L in colorectal cancer analyzed by immunohistochemistry with tissue microarray consists of 115 cancer specimens. Left panels: non-tumor tissues; right panels: colorectal tumors. Original magnification: ×400. (B) Representative images of the relative staining intensity of phospho-ERK and CSE1L in tumors analyzed by immunohistochemistry with adjacent serial colorectal cancer tissue sections. Arrowheads indicate coincidence in the relative staining intensity of phospho-ERK with CSE1L in tumors. Original magnification: ×40.
Figure 6:
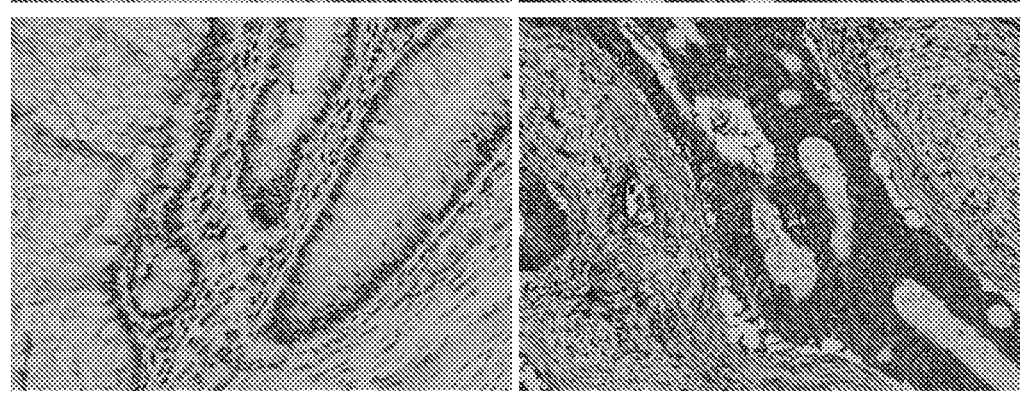
Figure 6:
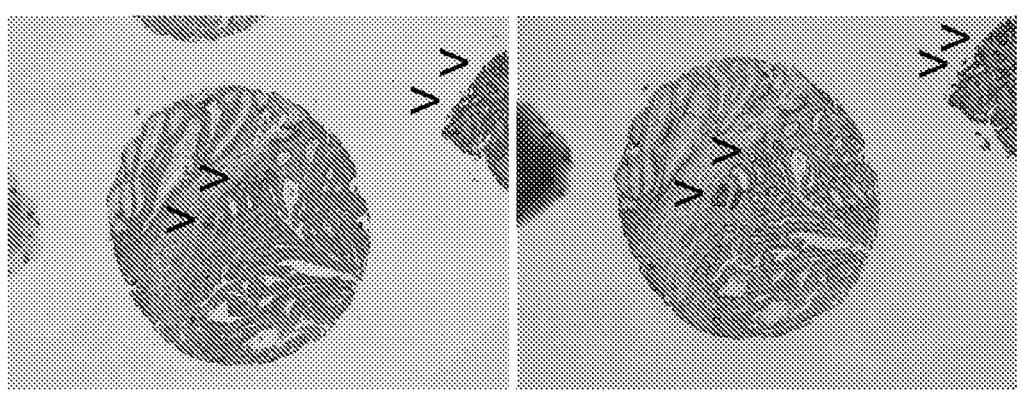

FIG. 6 shows high expression of phospho-ERK and CSE1L in colorectal cancer and coincidence in the relative staining intensity of phospho-ERK with CSE1L in tumors. (A) Expression of phospho-ERK and CSE1L in colorectal cancer analyzed by immunohistochemistry with tissue microarray consists of 115 cancer specimens. Left panels: non-tumor tissues; right panels: colorectal tumors. Original magnification: ×400. (B) Representative images of the relative staining intensity of phospho-ERK and CSE1L in tumors analyzed by immunohistochemistry with adjacent serial colorectal cancer tissue sections. Arrowheads indicate coincidence in the relative staining intensity of phospho-ERK with CSE1L in tumors. Original magnification: ×40.

Example 7

CSE1L Mediates v-H-ras-Induced Microvesicle Biogenesis in Cells

Microscopic examination showed there was no microvesicle present in the surfaces of B16-Ras/anti-CSE1L cells, the CSE1L shRNA plasmid-transfected B16-Ras cells (FIG. 7A). There was also no accumulation of developing microvesicles at the cytoplasm or the base of pseudopodia in B16-Ras/anti-CSE1L cells (FIG. 7A). Microscopic examination also showed the presence of microvesicles in the surfaces B16-CSE1L cells (FIG. 7B). Unlike microvesicles induced by v-H-ras, CSE1L induced fewer numbers of microvesicles per cell and the vesicles were larger in size and were mainly located in the tips of invadopodia of cells (FIG. 7B). These differences are reasonable since v-H-ras transfection stimulates ERK activation and ERK mediates both microvesicle generation and release. CSE1L overexpression only stimulates microvesicle generation; therefore microvesicles induced by CSE1L may accumulate in cell membrane and become bigger in size. Previous study has shown that vesicles are generated at the plasma membrane and move along filopodia toward the tips of filopodia (Bianco et al. 2005). CSE1L was stained in MMP-2-rich developing microvesicles that located at the base of pseudopodia (FIG. 7C). CSE1L was also stained in cytoplasmic developing microvesicles that located behind the shedding microvesicles in B16-Ras cells (FIG. 7C). Moreover, CSE1L shRNA inhibited v-H-ras-induced microvesicle generation (FIG. 7A). Thus, CSE1L is a regulator of microvesicle generation and it mediates v-H-ras-induced microvesicle generation.

Figure 7:
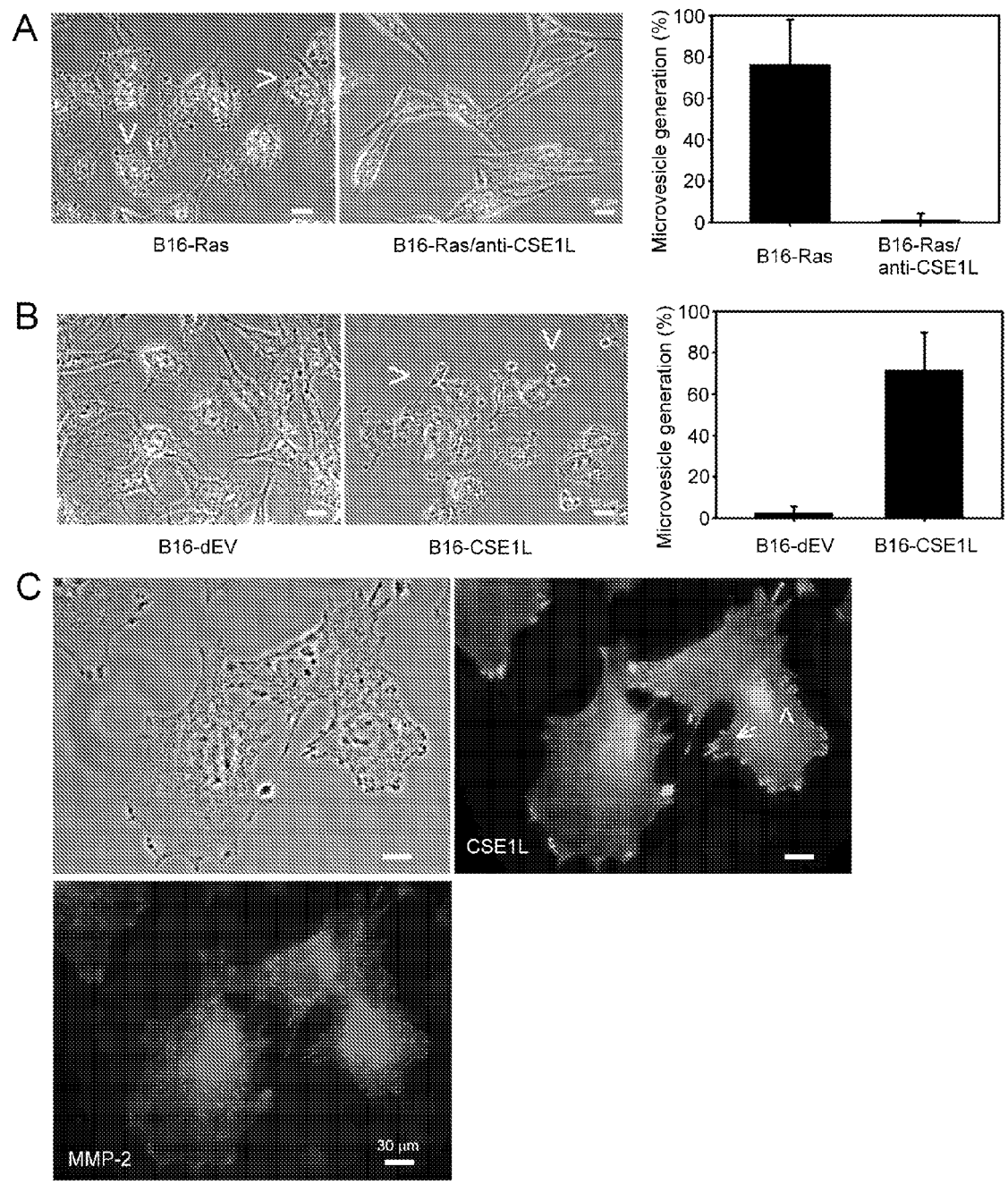
FIG. 7 refers to CSE1L mediates v-H-ras-induced microvesicle biogenesis of cells. (A) Inverted micrograph of B16-Ras and B16-Ras/anti-CSE1L cells grown on glass cover slides for 4 days. (B) Representative images of B16-dEV and B16-CSE1L cells grown on glass cover slides for 4 days. (C) Representative images of CSE1L and MMP-2 staining in developing microvesicles located at the base of pseudopodia (arrow) or cytoplasm (arrowhead).

FIG. 7 shows CSE1L mediates v-H-ras-induced microvesicle generation. (A) Inverted micrograph of B16-Ras and B16-Ras/anti-CSE1L cells grown on glass cover slides for 4 days. (B) Representative images of B16-dEV and B16-CSE1L cells grown on glass cover slides for 4 days. (C) Representative images of CSE1L and MMP-2 staining in developing microvesicles located at the base of pseudopodia (arrow) or cytoplasm behind shedding microvesicles (arrowhead).

Example 8

CSE1L Mediates the In Vitro Invasion of Tumor Cells Induced by v-H-ras

The results of gelatin zymography assay with microvesicles harvested form the cell number-standardized conditioned media of serum-starved B16-dEV, B16-Ras, B16-CSE1L, and B16-Ras/anti-CSE1L cells treated with or without DMSO or 50 µM PD98059 showed that v-H-ras transfection increased the zymographic activity of microvesicular MMP-2, and PD98059 treatment attenuated the v-H-ras-induced increase in the zymographic activity of microvesicular MMP-2 (FIG. 8A). CSE1L overexpression also increased the zymographic activity of microvesicular MMP-2, and CSE1L shRNA transfection attenuated the v-H-ras-induced increase in microvesicular MMP-2 zymographic activity (FIG. 8A). Matrigel-based invasion assay showed both v-H-Ras transfection and CSE1L overexpression increased the in vitro invasion of B16F10 cells and CSE1L shRNA transfection attenuated the v-H-Ras-induced increase in the invasion ability of the cells (FIG. 8B). Thus, CSE1L mediates the in vitro invasion of tumor cells induced by v-H-ras.

Figure 8:
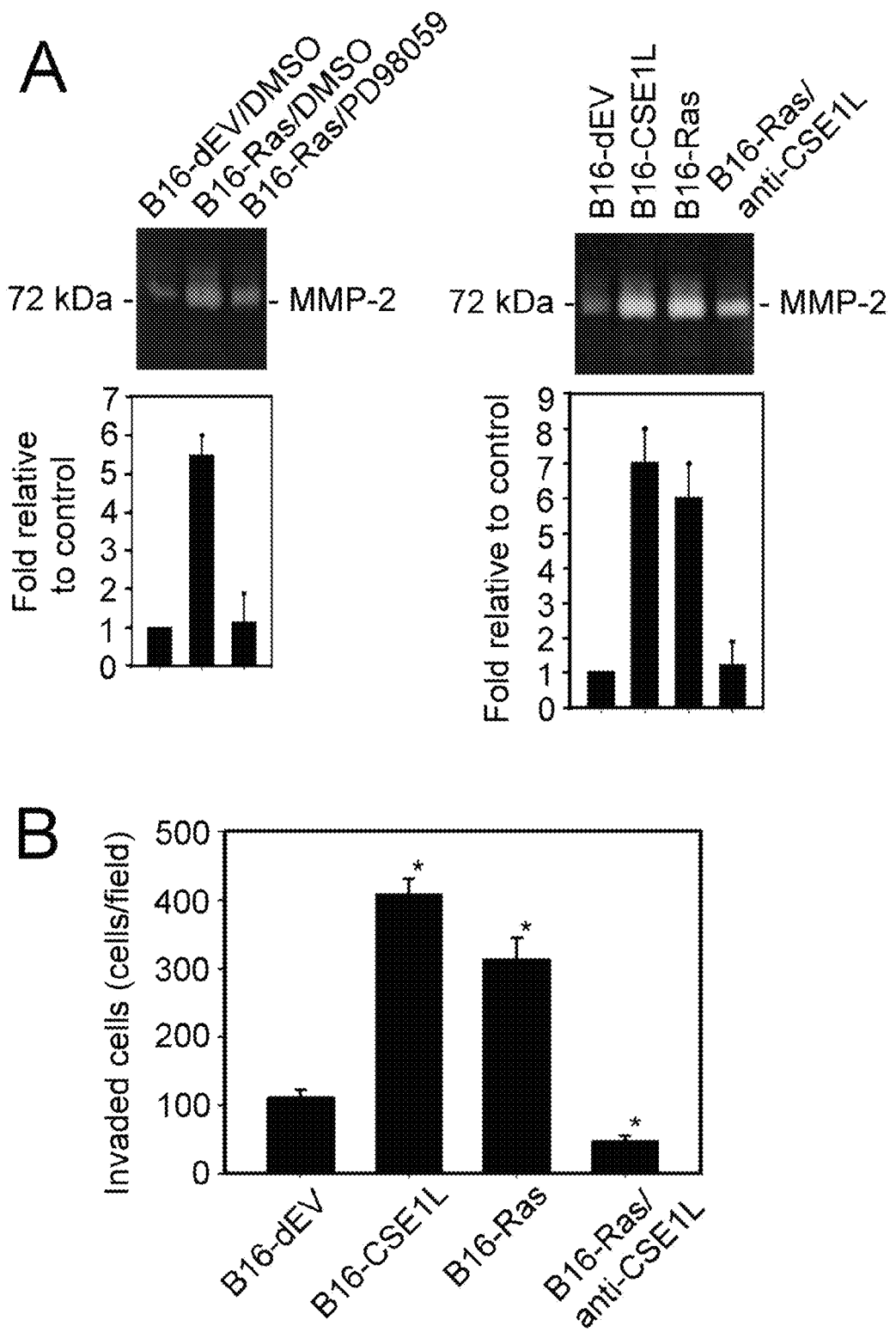
FIG. 8 refers to CSE1L mediates the in vitro invasion of tumor cells induced by v-H-ras. (A) Microvesicular MMP-2 zymographic activities of microvesicles harvested from the cell number-standardized conditioned media of serum-starved B16-dEV, B16-Ras, B16-CSE1L, and B16-Ras/anti-CSE1L cells treated with or without DMSO or 50 µM PD98059 for 24 h as indicated. (B) The in vitro invasion abilities of B16-dEV, B16-Ras, B16-CSE1L, and B16-Ras/anti-CSE1L cells analyzed by Matrigel-based invasion assays.

FIG. 8 shows CSE1L mediates the in vitro invasion of tumor cells induced by v-H-ras. (A) Gelatin zymographic activities of MMP-2 in microvesicles harvested form the cell number-standardized conditioned media of serum-starved B16-dEV, B16-Ras, B16-CSE1L, and B16-Ras/anti-CSE1L cells treated with or without DMSO or 50 µM PD98059 for 48 h as indicated. (B) The in vitro invasion abilities of B16-dEV, B16-Ras, B16-CSE1L, and B16-Ras/anti-CSE1L cells analyzed by Matrigel-based invasion assays. The mean±SD numbers of invasive cells were 109.4±12.6, 406.8±23.9, 311.25±32.4, and 46.75±8.7 cells per field for B16-dEV, B16-CSE1L, B16-Ras, and B16-Ras/anti-CSE1L cells, respectively.

Example 9

CSE1L Mediates v-H-ras-Induced Cancer Cell Metastasis

MMP-2 plays an essential role in tumor invasion (Taraboletti et al. 2002). Immunofluorescence showed CSE1L was colocalized with MMP-2 in microvesicles in the cell surfaces of B16-Ras and B16-CSE1L cells (FIG. 9A). Also, CSE1L was preferentially accumulated in microvesicles (FIG. 9A). The results of animal experimental studies showed CSE1L overexpression and v-H-Ras transfection increased the pulmonary metastasis of B16F10 cells by 361.5% ($P<0.01$) and 246.1% ($P<0.01$), respectively, in C57BL/6 mice; CSE1L shRNA transfection attenuated the v-H-Ras-induced increase in tumor pulmonary metastasis of the cells by 100% ($P<0.01$); although the growth rates of B16-Ras and B16-Ras/anti-CSE1L cells were similar (FIGS. 9B and C). Thus, CSE1L mediates the metastasis of tumor cells induced by v-H-Ras.

Figure 9:
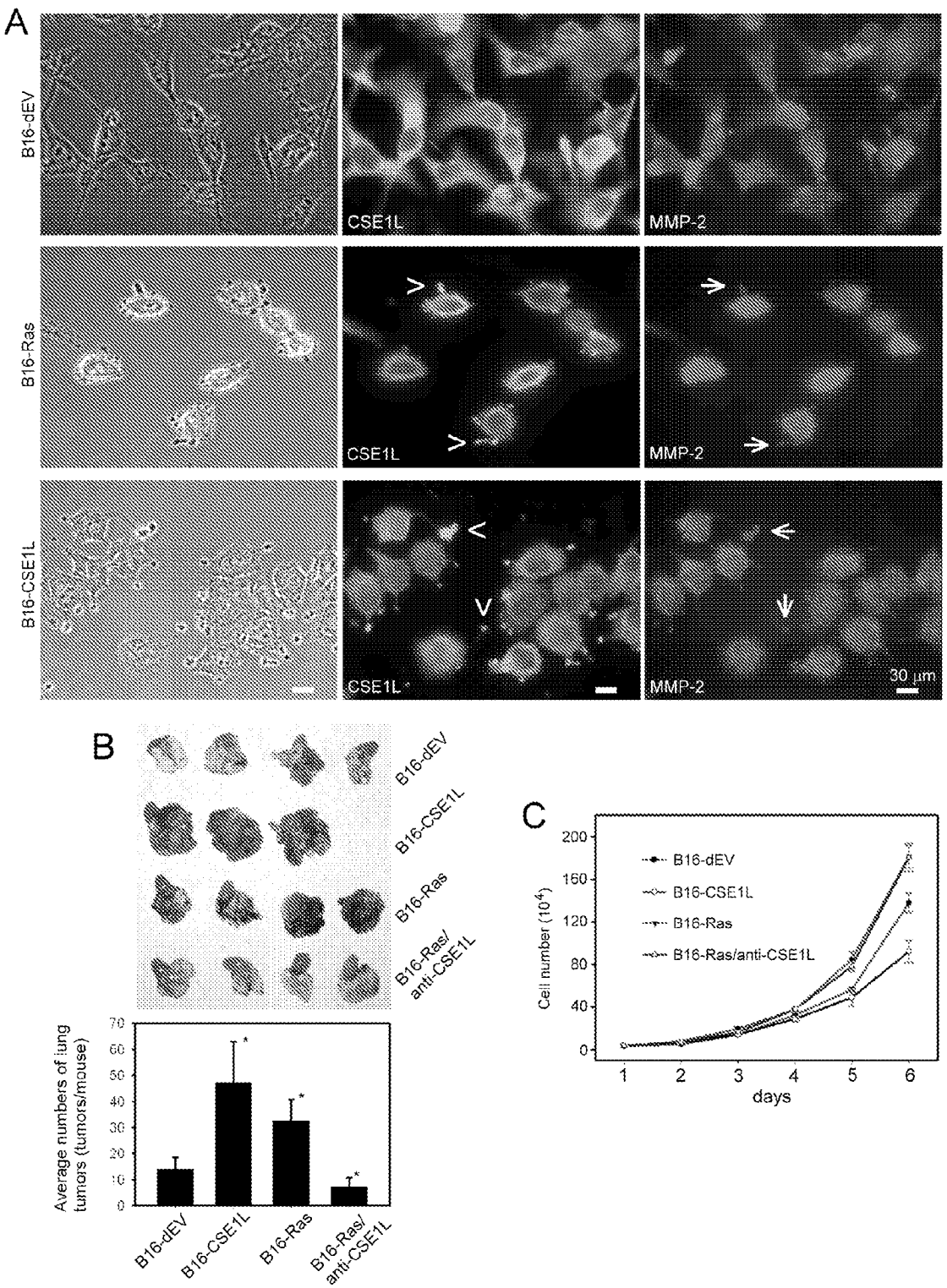
FIG. 9 refers to CSE1L mediates v-H-ras-induced cancer cell metastasis. (A) Immunofluorescences show colocalization of CSE1L and MMP-2 in microvesicles, and CSE1L was preferentially accumulated in microvesicles in B16-Ras and B16-CSE1L cells. (B) CSE1L mediates v-H-ras-induced cell metastasis. The upper is a representative photograph of the pulmonary tumors of C57BL/6 mice injected with B16-dEV, B16-Ras, B16-CSE1L, and B16-Ras/anti-CSE1L cells. (C) The growth curves of B16-dEV, B16-CSE1L, B16-Ras, and B16-Ras/anti-CSE1L cells. The graph represents the results of three independent assays.

FIG. 9 shows CSE1L mediates v-H-ras-induced cancer cell metastasis. (A) Representative immunofluorescences show colocalization of CSE1L and MMP-2 in microvesicles in B16-Ras and B16-CSE1L cells analyzed by immunofluorescence. Also, CSE1L was preferentially accumulated in microvesicles (arrowheads). MMP-2 distribution was used for comparison. (B) CSE1L mediates v-H-ras-induced cell metastasis. The upper is a representative photograph of the pulmonary tumors of C57BL/6 mice injected with B16-dEV B16-Ras, B16-CSE1L, and B16-Ras/anti-CSE1L cells. The mean±SD numbers of lung tumors were 13.7±4.8, 47±15.8, 32.2±8.5, and 7±3.6 tumors per mouse for mice injected with B16-dEV (N=7), B16-CSE1L (N=3), B16-Ras (N=4), and B16-Ras/anti-CSE1L cells (N=7), respectively. There were 3, 10, 4, and 1 mice died three weeks after injected with B16-dEV, B16-CSE1L, B16-Ras, and B16-Ras/anti-CSE1L cells, respectively, and thus were excluded from the statistics. There were 1, 1, 0, and 3 mice injected with B16-dEV, B16-CSE1L, B16-Ras, and B16-Ras/anti-CSE1L cells, respectively, that did not grow tumor in the lungs, and thus were also excluded from the statistics. (C) The growth curves of B16-dEV, B16-CSE1L, B16-Ras, and B16-Ras/anti-CSE1L cells. The graph represents the results of three independent assays.

Example 10

CSE1L is Localized in Microvesicle Membrane and Anti-CSE1L Antibodies can Target Tumor The results of immunofluorescence showed CSE1L was located in microvesicle membrane (FIG. 10A). Immunogold electron microscopy further showed CSE1L and MMP-2 were located in vesicle and CSE1L was mainly located in the vesicle membrane (FIG. 10B). Shedding microvesicles are widespread on the membrane of tumor cells and the shed microvesicles may remain in the extracellular environment around tumor cells; hence, microvesicle membrane proteins may be the potential targets for cancer therapy. The localization of CSE1L in microvesicle membrane indicates that CSE1L may be a therapeutic target for cancer. C57BL/6 mice bearing tumors were injected with Qdot 800 nanocrystals-conjugated anti-CSE1L antibodies or Qdot 800 nanocrystals-conjugated anti-mouse IgG as the control in the tail vain. The results of in vivo imaging showed the presence of significant near-infrared (NIR) fluorescence signal in tumor of mouse injected with anti-CSE1L antibodies-conjugated quantum dots but not in tumor of mouse injected with control IgG-conjugated quantum dots (FIG. 10C). Thus, anti-CSE1L antibodies can target tumor.

Figure 10:
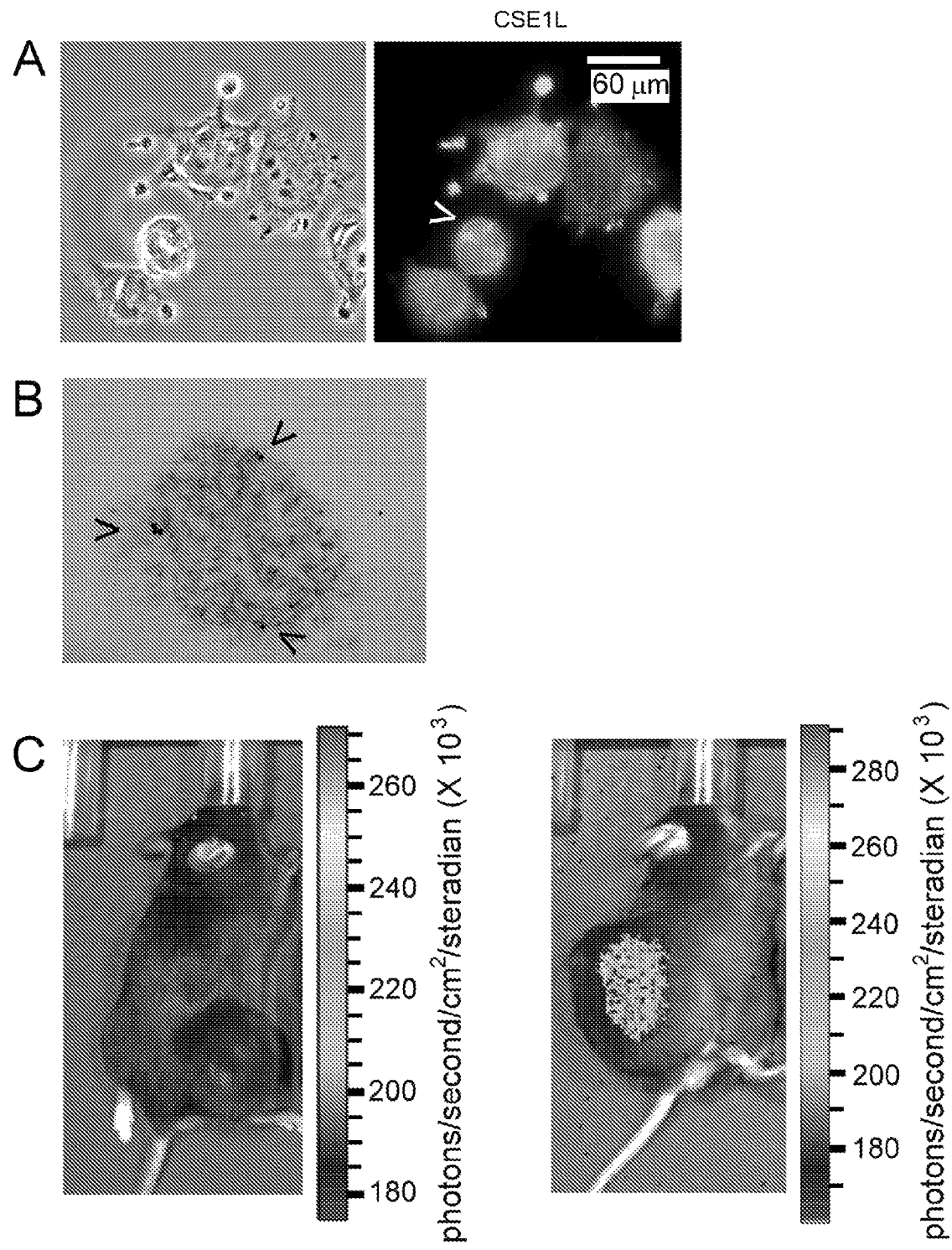
FIG. 10 refers to CSE1L is localized in microvesicle membrane and anti-CSE1L antibodies can target tumor. (A) CSE1L localization in microvesicle membrane (arrowhead) in B16-CSE1L cells analyzed by immunofluorescence. (B) Immunogold electron microscopy analysis of CSE1L (18-nm gold, arrowhead) and MMP-2 (12-nm gold) distribution in microvesicle in B16-CSE1L cells. Original magnification: ×250,000. (C) Composite images show the NIR fluorescence signals of C57BL/6 mice bearing B16-CSE1L cells-derived tumor xenografts injected with quantum dots-conjugated anti-CSE1L antibodies (right, N=3) or quantum dots-conjugated anti-mouse IgG (left, N=3) at 4 h post-injection. The NIR images were acquired and processed under the same conditions.

FIG. 10 shows CSE1L is localized in microvesicle membrane and anti-CSE1L antibodies can target tumor. (A) CSE1L localization in microvesicle membrane (arrowhead) in B16-CSE1L cells analyzed by immunofluorescence. (B) Immunogold electron microscopy analysis of CSE1L (18-nm gold, arrowhead) and MMP-2 (12-nm gold) distribution in microvesicle in B16-CSE1L cells. Original magnification: ×250,000. (C) Composite images show the NIR fluorescence signals of C57BL/6 mice bearing B16-CSE1L cells-derived tumor xenografts injected with quantum dots-conjugated anti-CSE1L antibodies (right, N=3) or quantum dots-conjugated anti-mouse IgG (left, N=3) at 4 h post-injection. The NIR images were acquired and processed under the same conditions.

Example 11

Anti-phospho-CSE1L Antibody Reacts with Phosphorylated CSE1L

Figure 11:
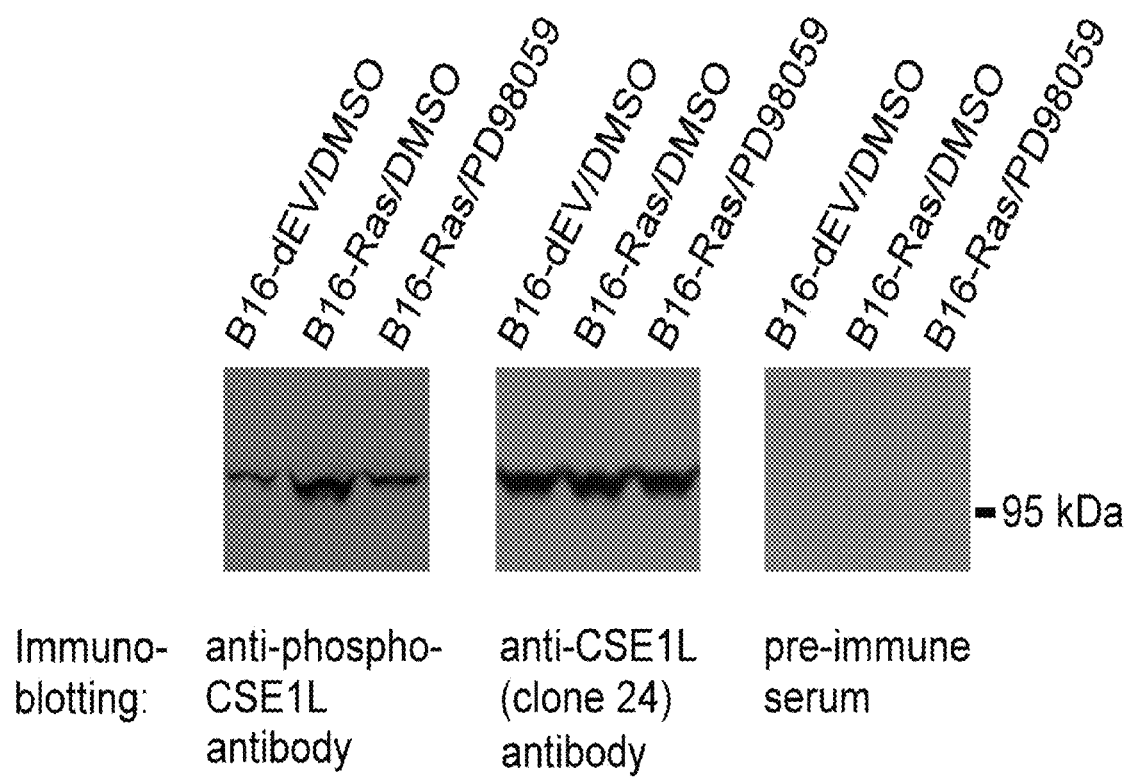
FIG. 11 refers to anti-phospho-CSE1L antibodies react with phosphorylated CSE1L. Characterization of the specificity of anti-phosphorylated CSE1L antibodies was performed by immunoblotting with cell lysates from B16-dEV and B16-Ras cells treated with DMSO or 50 µM PD98059 for 12 h.

Antibodies specific to phospho-CSE1L was produced by immunizing New-Zealand rabbits with synthetic phosphopeptides designed to correspond to the putative phosphorylation domain of CSE1L. The titer of the affinity purified anti-phospho-CSE1L antibodies were determined by indirect ELISA (Table 2). The results of immunoblotting showed the anti-phospho-CSE1L antibodies react with phosphorylated CSE1L (FIG. 11).

Table 2 shows the titer of the affinity purified anti-phospho-CSE1L antibodies determined by indirect ELISA.

TABLE 2

The titer of the affinity purified anti-phospho-CSE1L antibodies determined by indirect ELISA.

| Antibody concentration | Coating peptides | |
|---|---|---|
| | Phosphopeptide | Non-phosphopeptide |
| 80 ng/ml | 2.129* | 0.064 |
| 40 ng/ml | 0.624 | 0.054 |
| 20 ng/ml | 0.201 | 0.050 |
| 10 ng/ml | 0.081 | 0.041 |
| 5 ng/ml | 0.053 | 0.041 |
| 2.5 ng/ml | 0.046 | 0.037 |
| 1.25 ng/ml | 0.043 | 0.032 |
| PBS | 0.035 | 0.032 |

*O.D (optical density).

FIG. 11 shows the anti-phospho-CSE1L antibodies react with phosphorylated CSE1L. Characterization of the specificity of the anti-phospho-CSE1L antibodies was performed by immunoblotting with equal amount (50 μg) cell lysates from B16-dEV and B16-Ras cells treated with DMSO or 50 μM PD98059 for 12 h. The anti-CSE1L antibodies (clone 24) and the pre-immune serum of the animal were used as the control.

Example 12

Phosphorylated CSE1L is Localized in Microvesicles

Whether phosphorylated CSE1L was localized in microvesicles was analyzed. The results of immunofluorescence with anti-phospho-CSE1L antibodies showed phosphorylated CSE1L were localized in microvesicles (arrowheads) (FIG. 12).

Figure 12:
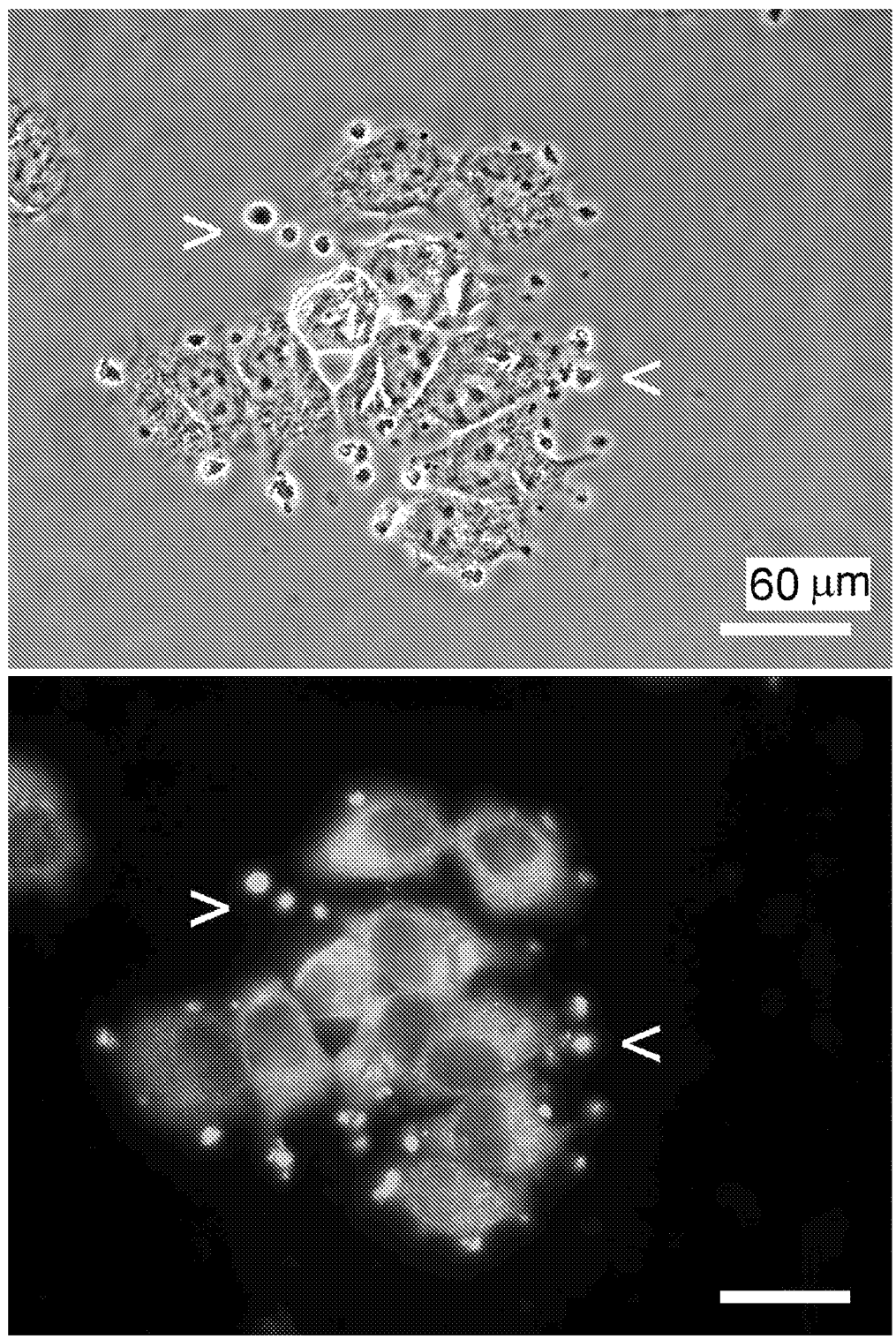
FIG. 12 refers to phosphorylated CSE1L is localized in microvesicles. Localization of phosphorylated CSE1L in microvesicles (arrowheads) in B16-CSE1L cells assayed by immunofluorescence with anti-phospho-CSE1L antibodies.

FIG. 12 shows localization of phosphorylated CSE1L in microvesicles (arrowheads) in B16-CSE1L cells analyzed by immunofluorescence with anti-phospho-CSE1L antibodies.

Example 13

Presence of CSE1L in Microvesicles Isolated from Cancer Sera

Microvesicles were isolated from the sera of colorectal cancer patients and healthy donors. The isolated microvesicles were applied to a 96-well dot-blot manifold (BRL, Bethesda, Md., USA) and the presence of CSE1L in serum microvesicles were assayed with by dot blots with anti-CSE1L antibodies and anti-phospho-CSE1L antibodies. The intensities of the blots were quantified by using an IS-1000 Digital Imaging System (Kaiser Alpha Innotech, USA). The results showed higher prevalence of phosphorylated CSE1L in microvesicles isolated from cancer sera samples than that isolated from normal sera samples. The results also showed higher prevalence of CSE1L in microvesicles isolated from the cancer sera samples than that isolated from normal sera samples. CSE1L was detected in 96.5% (111/115) of sera microvesicles from cancer patients and was detected in 6.6% (4/60) of serum microvesicles from healthy donors. The P-values were <0.01 between the cancer group and healthy group. With the use of the synthesized CSE1L as a standard, the cut-off value of CSE1L in the serum microvesicles from cancer patients was determined to be >21 ng/ml. The phosphorylated CSE1L was detected in 98.2% (113/115) of sera microvesicles from the cancer patients and was detected in 3.3% (2/60) of serum microvesicles from healthy donors. The P-values were <0.01 between the cancer group and healthy group. With the use of the phosphorylated CSE1L peptides as a standard, the cut-off value of phosphorylated CSE1L in the serum microvesicles from cancer patients was determined to be >15 ng/ml.

Example 14

Higher Prevalence of Phosphorylated CSE1L in Sera of Cancer Patients and Assay of Phosphorylated CSE1L in Sera is Superior to Assay of CSE1L for Cancer Diagnosis The results showed the presence of phosphorylated CSE1L in microvesicles isolated from cancer sera (Example 13). The results of immunoprecipitations also showed the presence of phosphorylated CSE1L in the immunoprecipitates from cancer sera samples but not from normal sera samples (FIG. 5C). The prevalence of CSE1L and phosphorylated CSE1L in sera from colorectal cancer patients were analyzed. The results of ELISA showed that 92.1% (106/115) of the cancer sera were phosphorylated CSE1L-positive, and only 1.6% (1/60) of sera from healthy donors were phosphorylated CSE1L-positive. The P-values were <0.01 between the cancer group and healthy group. With the use of the phosphorylated CSE1L peptides as a standard, the cut-off value of phosphorylated CSE1L in the sera of cancer patients was determined to be ≧3 ng/ml. The results of ELISA showed that 65.2% (75/115) of the cancer sera were CSE1L-positive, and 13% (8/60) of sera from healthy donors were CSE1L-positive. With the use of the synthesized CSE1L as a standard, the cut-off value of CSE1L in the sera of cancer patients was determined to be ≧8 ng/ml. The sensitivity and specificity of serum phosphorylated CSE1L for detection of the cancer were 92.1% and 98.3%, respectively. The sensitivity and specificity of serum CSE1L for detection of the cancer were 65.2% and 86.6%, respectively. Therefore, assay of serum phosphorylated CSE1L is superior to assay of serum CSE1L for cancer diagnosis.

REFERENCE

1. Bianco F, Pravettoni E, Colombo A, Schenk U, Möller T, Matteoli M, Verderio C. Astrocyte-derived ATP induces vesicle shedding and IL-1 beta release from microglia. J Immunol 2005; 174:7268-7277.
2. Brinkmann U, Brinkmann E, Gallo M, Pastan I. Cloning and characterization of a cellular apoptosis susceptibility gene, the human homologue to the yeast chromosome segregation gene CSE1. Proc Natl Acad Sci USA 1995; 92:10427-10431.
3. Cocucci E, Racchetti G, Meldolesi J. Shedding microvesicles: artefacts no more. Trends Cell Biol 2009; 19:43-51.
4. Hoshino R, Chatani Y, Yamori T, Tsuruo T, Oka H, Yoshida O, Shimada Y, Ari-i S, Wada H, Fujimoto J, Kohno M. Constitutive activation of the 41-/43-kDa mitogen-activated protein kinase signaling pathway in human tumors. Oncogene 1999; 18:813-822.
5. Muralidharan-Chari V, Clancy J, Plou C, Romao M, Chavrier P, Raposo G, D'Souza-Schorey C. ARF6-regulated shedding of tumor cell-derived plasma membrane microvesicles. Curr Biol 2009; 19:1875-1885.
6. Muralidharan-Chari V, Clancy J W, Sedgwick A, D'Souza-Schorey C. Microvesicles: mediators of extracellular communication during cancer progression. J Cell Sci 2010; 123:1603-1611.
7. Roberts P J, Der C J. Targeting the Raf-MEK-ERK mitogen-activated protein kinase cascade for the treatment of cancer. Oncogene 2007; 26:3291-3310.
8. Scherf U, Kalab P, Dasso M, Pastan I, Brinkmann U. The hCSE1/CAS protein is phosphorylated by HeLa extracts and MEK-1: MEK-1 phosphorylation may modulate the intracellular localization of CAS. Biochem Biophys Res Commun 1998; 250:623-628.
9. Simak J, Gelderman MP. Cell membrane microparticles in blood and blood products: potentially pathogenic agents and diagnostic markers. Transfus Med Rev 2006; 20:1-26.
10. Tai C J, Hsu C H, Shen S C, Lee W R, Jiang M C. Cellular apoptosis susceptibility (CSE1L/CAS) protein in cancer metastasis and chemotherapeutic drug-induced apoptosis. J Exp Clin Cancer Res 2010; 29:110.
11. Taraboletti G, D'Ascenzo S, Borsotti P, Giavazzi R, Pavan A, Dolo V. Shedding of the matrix metalloproteinases MMP-2, MMP-9, and MT1-MMP as membrane vesicle-associated components by endothelial cells. Am J Pathol 2002; 160:673-680.
12. Tung M C, Tsai C S, Tung J N, Tsao T Y, Chen H C, Yeh K T, Liao C F, Jiang M C. Higher prevalence of secretory CSE1L/CAS in sera of patients with metastatic cancer. Cancer Epidemiol Biomarkers Prev 2009; 18:1570-1577.
13. van Doormaal F F, Kleinjan A, Di Nisio M, Büller HR, Nieuwland R. Cell-derived microvesicles and cancer. Neth J Med 2009; 67:266-273.

What is claimed is:

1. An in vitro method of measuring the levels of chromosome segregation 1-like protein (CSE1L) or phosphorylated CSE1L in microvesicles in biological fluid of a test subject comprising the steps of:
   (a) obtaining a test biological fluid sample from a test subject;
   (b) isolating microvesicles in the test biological fluid sample;
   (c) contacting the microvesicles with an antibody against CSE1L or an antibody that specifically recognizes phosphorylated CSE1L and does not recognize non-phosphorylated CSE1L; and
   (d) determining the amount of CSE1L or phosphorylated CSE1L in microvesicles in the test biological fluid sample.

2. The method of claim 1, wherein the amount of CSE1L or phosphorylated CSE1L is measured by assaying the microvesicles with a dot blot assay.

3. The method of claim 1, wherein the amount of CSE1L is measured by assaying the binding between an anti-CSE1L antibody and CSE1L; and the amount of phosphorylated CSE1L is measured by assaying the binding between an anti-phosphorylated CSE1L antibody and phosphorylated CSE1L.

4. The method of claim 1, wherein the subject is a human.

5. An in vitro method of measuring the level of phosphorylated CSE1L in body fluids from a test subject comprising the steps of:
   (a) obtaining a test biological fluid sample from a test subject;
   (b) contacting the test biological fluid sample with an antibody that specifically recognizes phosphorylated CSE1L and does not recognize non-phosphorylated CSE1L; and
   (c) determining the amount of phosphorylated CSE1L in the test biological fluid sample.

6. The method of claim 5, wherein the amount of phosphorylated CSE1L is measured by assaying said sample with an enzyme-linked immunosorbent assay (ELISA).

7. The method of claim 5, wherein the amount of phosphorylated CSE1L is measured by assaying the binding between an anti-phosphorylated CSE1L antibody and phosphorylated CSE1L.

8. The method of claim 5, wherein the subject is a human.

9. The method of claim 1, wherein the presence of microvesicles in the biological fluid sample is assayed by immunological techniques, wherein the biological fluid sample is contacted in vitro with the antibody against CSE1L or the antibody that specifically recognizes phosphorylated CSE1L and does not recognize non-phosphorylated CSE1L, and wherein the binding of the antibody with microvesicles indicates the presence of microvesicles in the biological fluid sample.

* * * * *

SEQUENCE LISTING

<160> NUMBER OF SEQ ID NOS: 3

<210> SEQ ID NO 1
<211> LENGTH: 3147
<212> TYPE: DNA
<213> ORGANISM: Homo sapiens

<400> SEQUENCE: 1

```
gtcgcgccat tttgccgggg tttgaatgtg aggcggagcg gcggcaggag cggatagtgc      60
cagctacggt ccgcggctgg ggttccctcc tccgtttctg tatccccacg agatcctata     120
gcaatggaac tcagcgatgc aaatctgcaa acactaacag aatatttaaa gaaaacactt     180
```

```
gatcctgatc ctgccatccg acgtccagct gagaaatttc ttgaatctgt tgaaggaaat    240
cagaattatc cactgttgct tttgacatta ctggagaagt cccaggataa tgttatcaaa    300
gtatgtgctt cagtaacatt caaaaactat attaaaagga actggagaat gttgaagat     360 gaaccaaaca aaatttgtga agccgatcga gtggccatta agccaacat agtgcacttg     420 atgcttagca gcccagagca aattcagaag cagttaagtg atgcaattag cattattggc    480
agagaagatt ttccacagaa atggcctgac ttgctgacag aaatggtgaa tcgctttcag    540
agtggagatt tccatgttat taatggagtc ctccgtacag cacattcatt atttaaaaga    600
taccgtcatg aatttaagtc aaacgagtta tggactgaaa ttaagcttgt tctggatgcc    660
tttgctttgc ctttgactaa tcttttaag gccactattg aactctgcag tacccatgca     720
aatgatgcct ctgccctgag gattctgttt tcttccctga tcctgatctc aaaattgttc    780
tatagtttaa actttcagga tctccctgaa ttttgggaag gtaatatgga aacttggatg    840
aataatttcc atactctctt aacattggat aataagcttt tacaaactga tgatgaagag    900
gaagccggct tattggagct cttaaaatcc cagatttgtg ataatgccgc actctatgca    960
caaaagtacg atgaagaatt ccagcgatac ctgcctcgtt ttgttacagc catctggaat   1020
ttactagtta caacgggtca agaggttaaa tatgatttgt tggtaagtaa tgcaattcaa   1080
tttctggctt cagtttgtga gagacctcat tataagaatc tatttgagga ccagaacacg   1140
ctgacaagta tctgtgaaaa ggttattgtg cctaacatgg aatttagagc tgctgatgaa   1200
gaagcatttg aagataattc tgaggagtac ataaggagag atttggaagg atctgatatt   1260
gatactagac gcagggctgc ttgtgatctg gtacgaggat tatgcaagtt ttttgaggga   1320
cctgtgacag gaatcttctc tggttatgtt aattccatgc tgcaggaata cgcaaaaaat   1380
ccatctgtca actggaaaca caaagatgca gccatctacc tagtgacatc tttggcatca   1440
aaagcccaaa cacagaagca tggaattaca caagcaaatg aacttgtaaa cctaactgag   1500
ttctttgtga atcacatcct ccctgattta aaatcagcta atgtgaatga atttcctgtc   1560
cttaaagctg acggtatcaa atatattatg attttagaa atcaagtgcc aaaagaacat    1620
cttttagtct cgattcctct cttgattaat catcttcaag ctggaagtat tgttgttcat   1680
acttacgcag ctcatgctct tgaacggctc tttactatgc gagggcctaa caatgccact   1740
ctctttacag ctgcagaaat cgcaccgttt gttgagattc tgctaacaaa ccttttcaaa   1800
gctctcacac ttcctggctc ttcagaaaat gaatatatta tgaaagctat catgagaagt   1860
ttttctctcc tacaagaagc cataatcccc tacatcccta ctctcatcac tcagcttaca   1920
cagaagctat tagctgttag taagaaccca agcaaacctc actttaatca ctacatgttt   1980
gaagcaatat gtttatccat aagaataact tgcaaagcta accctgctgc tgttgtaaat   2040
tttgaggagg ctttgttttt ggtgtttact gaaatcttac aaaatgatgt gcaagaattt   2100
attccatacg tctttcaagt gatgtctttg cttctggaaa cacacaaaaa tgacatcccg   2160
tcttcctata tggccttatt tcctcatctc cttcagccag tgctttggga agaacagga    2220 aatattcctg ctctagtgag gcttcttcaa gcattcttag aacgcggttc aaacacaata   2280
gcaagtgctg cagctgacaa aattcctggg ttactaggtg tctttcagaa gctgattgca   2340
tccaaagcaa atgaccacca aggtttttat cttctaaaca gtataataga gcacatgcct   2400
cctgaatcag ttgaccaata taggaaacaa atcttcattc tgctattcca gagacttcag   2460
aattccaaaa caaccaagtt tatcaagagt ttttagtct ttattaattt gtattgcata    2520
aaatatgggg cactagcact acaagaaata tttgatggta tacaaccaaa aatgtttgga   2580
```

-continued

```
atggttttgg aaaaaattat tattcctgaa attcagaagg tatctggaaa tgtagagaaa    2640
aagatctgtg cggttggcat aaccaactta ctaacagaat gtcccccaat gatggacact    2700
gagtatacca aactgtggac tccattatta cagtctttga ttggtctttt tgagttaccc    2760
gaagatgata ccattcctga tgaggaacat tttattgaca tagaagatac accaggatat    2820
cagactgcct tctcacagtt ggcatttgct gggaaaaaag agcatgatcc tgtaggtcaa    2880
atggtgaata ccccaaaat tcacctggca cagtcacttc acatgttgtc taccgcctgt    2940
ccaggaaggg ttccatcaat ggtgagcacc agcctgaatg cagaagcgct ccagtatctc    3000
caagggtacc ttcaggcagc cagtgtgaca ctgctttaaa ctgcattttt ctaatgggct    3060
aaacccagat ggtttcctag gaaatcacag gcttctgagc acagctgcat aaaacaaag    3120 gaagttttcc ttttgaactt gtcacga                                        3147
```

<210> SEQ ID NO 2
<211> LENGTH: 971
<212> TYPE: PRT
<213> ORGANISM: Homo sapiens

<400> SEQUENCE: 2

```
Met Glu Leu Ser Asp Ala Asn Leu Gln Thr Leu Thr Glu Tyr Leu Lys
 1               5                  10                  15

Lys Thr Leu Asp Pro Asp Pro Ala Ile Arg Arg Pro Ala Glu Lys Phe
            20                  25                  30

Leu Glu Ser Val Glu Gly Asn Gln Asn Tyr Pro Leu Leu Leu Leu Thr
        35                  40                  45

Leu Leu Glu Lys Ser Gln Asp Asn Val Ile Lys Val Cys Ala Ser Val
    50                  55                  60

Thr Phe Lys Asn Tyr Ile Lys Arg Asn Trp Arg Ile Val Glu Asp Glu
65                  70                  75                  80

Pro Asn Lys Ile Cys Glu Ala Asp Arg Val Ala Ile Lys Ala Asn Ile
                85                  90                  95

Val His Leu Met Leu Ser Ser Pro Glu Gln Ile Gln Lys Gln Leu Ser
            100                 105                 110

Asp Ala Ile Ser Ile Ile Gly Arg Glu Asp Phe Pro Gln Lys Trp Pro
        115                 120                 125

Asp Leu Leu Thr Glu Met Val Asn Arg Phe Gln Ser Gly Asp Phe His
    130                 135                 140

Val Ile Asn Gly Val Leu Arg Thr Ala His Ser Leu Phe Lys Arg Tyr
145                 150                 155                 160

Arg His Glu Phe Lys Ser Asn Glu Leu Trp Thr Glu Ile Lys Leu Val
                165                 170                 175

Leu Asp Ala Phe Ala Leu Pro Leu Thr Asn Leu Phe Lys Ala Thr Ile
            180                 185                 190

Glu Leu Cys Ser Thr His Ala Asn Asp Ala Ser Ala Leu Arg Ile Leu
        195                 200                 205

Phe Ser Ser Leu Ile Leu Ile Ser Lys Leu Phe Tyr Ser Leu Asn Phe
    210                 215                 220

Gln Asp Leu Pro Glu Phe Trp Glu Gly Asn Met Glu Thr Trp Met Asn
225                 230                 235                 240

Asn Phe His Thr Leu Leu Thr Leu Asp Asn Lys Leu Leu Gln Thr Asp
                245                 250                 255

Asp Glu Glu Glu Ala Gly Leu Leu Glu Leu Leu Lys Ser Gln Ile Cys
            260                 265                 270

Asp Asn Ala Ala Leu Tyr Ala Gln Lys Tyr Asp Glu Glu Phe Gln Arg
```

```
                275                 280                 285
Tyr Leu Pro Arg Phe Val Thr Ala Ile Trp Asn Leu Leu Val Thr Thr
290                 295                 300
Gly Gln Glu Val Lys Tyr Asp Leu Leu Val Ser Asn Ala Ile Gln Phe
305                 310                 315                 320
Leu Ala Ser Val Cys Glu Arg Pro His Tyr Lys Asn Leu Phe Glu Asp
                325                 330                 335
Gln Asn Thr Leu Thr Ser Ile Cys Glu Lys Val Ile Val Pro Asn Met
                340                 345                 350
Glu Phe Arg Ala Ala Asp Glu Glu Ala Phe Glu Asp Asn Ser Glu Glu
                355                 360                 365
Tyr Ile Arg Arg Asp Leu Glu Gly Ser Asp Ile Asp Thr Arg Arg Arg
370                 375                 380
Ala Ala Cys Asp Leu Val Arg Gly Leu Cys Lys Phe Phe Glu Gly Pro
385                 390                 395                 400
Val Thr Gly Ile Phe Ser Gly Tyr Val Asn Ser Met Leu Gln Glu Tyr
                405                 410                 415
Ala Lys Asn Pro Ser Val Asn Trp Lys His Lys Asp Ala Ala Ile Tyr
                420                 425                 430
Leu Val Thr Ser Leu Ala Ser Lys Ala Gln Thr Gln Lys His Gly Ile
                435                 440                 445
Thr Gln Ala Asn Glu Leu Val Asn Leu Thr Glu Phe Phe Val Asn His
                450                 455                 460
Ile Leu Pro Asp Leu Lys Ser Ala Asn Val Asn Glu Phe Pro Val Leu
465                 470                 475                 480
Lys Ala Asp Gly Ile Lys Tyr Ile Met Ile Phe Arg Asn Gln Val Pro
                485                 490                 495
Lys Glu His Leu Leu Val Ser Ile Pro Leu Leu Ile Asn His Leu Gln
                500                 505                 510
Ala Gly Ser Ile Val Val His Thr Tyr Ala Ala His Ala Leu Glu Arg
                515                 520                 525
Leu Phe Thr Met Arg Gly Pro Asn Asn Ala Thr Leu Phe Thr Ala Ala
530                 535                 540
Glu Ile Ala Pro Phe Val Glu Ile Leu Leu Thr Asn Leu Phe Lys Ala
545                 550                 555                 560
Leu Thr Leu Pro Gly Ser Ser Glu Asn Glu Tyr Ile Met Lys Ala Ile
                565                 570                 575
Met Arg Ser Phe Ser Leu Leu Gln Glu Ala Ile Ile Pro Tyr Ile Pro
                580                 585                 590
Thr Leu Ile Thr Gln Leu Thr Gln Lys Leu Leu Ala Val Ser Lys Asn
                595                 600                 605
Pro Ser Lys Pro His Phe Asn His Tyr Met Phe Glu Ala Ile Cys Leu
                610                 615                 620
Ser Ile Arg Ile Thr Cys Lys Ala Asn Pro Ala Ala Val Val Asn Phe
625                 630                 635                 640
Glu Glu Ala Leu Phe Leu Val Phe Thr Glu Ile Leu Gln Asn Asp Val
                645                 650                 655
Gln Glu Phe Ile Pro Tyr Val Phe Gln Val Met Ser Leu Leu Leu Glu
                660                 665                 670
Thr His Lys Asn Asp Ile Pro Ser Ser Tyr Met Ala Leu Phe Pro His
                675                 680                 685
Leu Leu Gln Pro Val Leu Trp Glu Arg Thr Gly Asn Ile Pro Ala Leu
                690                 695                 700
```

-continued

```
Val Arg Leu Leu Gln Ala Phe Leu Glu Arg Gly Ser Asn Thr Ile Ala
705                 710                 715                 720

Ser Ala Ala Ala Asp Lys Ile Pro Gly Leu Leu Gly Val Phe Gln Lys
            725                 730                 735

Leu Ile Ala Ser Lys Ala Asn Asp His Gln Gly Phe Tyr Leu Leu Asn
        740                 745                 750

Ser Ile Ile Glu His Met Pro Pro Glu Ser Val Asp Gln Tyr Arg Lys
    755                 760                 765

Gln Ile Phe Ile Leu Leu Phe Gln Arg Leu Gln Asn Ser Lys Thr Thr
770                 775                 780

Lys Phe Ile Lys Ser Phe Leu Val Phe Ile Asn Leu Tyr Cys Ile Lys
785                 790                 795                 800

Tyr Gly Ala Leu Ala Leu Gln Glu Ile Phe Asp Gly Ile Gln Pro Lys
            805                 810                 815

Met Phe Gly Met Val Leu Glu Lys Ile Ile Pro Glu Ile Gln Lys
        820                 825                 830

Val Ser Gly Asn Val Glu Lys Lys Ile Cys Ala Val Gly Ile Thr Asn
    835                 840                 845

Leu Leu Thr Glu Cys Pro Pro Met Met Asp Thr Glu Tyr Thr Lys Leu
850                 855                 860

Trp Thr Pro Leu Leu Gln Ser Leu Ile Gly Leu Phe Glu Leu Pro Glu
865                 870                 875                 880

Asp Asp Thr Ile Pro Asp Glu Glu His Phe Ile Asp Ile Glu Asp Thr
            885                 890                 895

Pro Gly Tyr Gln Thr Ala Phe Ser Gln Leu Ala Phe Ala Gly Lys Lys
        900                 905                 910

Glu His Asp Pro Val Gly Gln Met Val Asn Asn Pro Lys Ile His Leu
    915                 920                 925

Ala Gln Ser Leu His Met Leu Ser Thr Ala Cys Pro Gly Arg Val Pro
930                 935                 940

Ser Met Val Ser Thr Ser Leu Asn Ala Glu Ala Leu Gln Tyr Leu Gln
945                 950                 955                 960

Gly Tyr Leu Gln Ala Ala Ser Val Thr Leu Leu
            965                 970

<210> SEQ ID NO 3
<211> LENGTH: 15
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: PHOSPHORYLATION
<220> FEATURE:
<221> NAME/KEY: MOD_RES
<222> LOCATION: (4)..(4)
<223> OTHER INFORMATION: PHOSPHORYLATION

<400> SEQUENCE: 3

Leu Thr Glu Tyr Leu Lys Lys Thr Leu Asp Pro Asp Pro Ala Cys
1               5                   10                  15
```